(12) United States Patent
Childs

(10) Patent No.: US 11,950,812 B2
(45) Date of Patent: Apr. 9, 2024

(54) SLEEVE FOR BONE FIXATION DEVICE

(71) Applicant: Ronald C. Childs, McLean, VA (US)

(72) Inventor: Ronald C. Childs, McLean, VA (US)

( * ) Notice: Subject to any disclaimer, the term of this patent is extended or adjusted under 35 U.S.C. 154(b) by 450 days.

(21) Appl. No.: 16/912,740

(22) Filed: Jun. 26, 2020

(65) Prior Publication Data

US 2020/0323565 A1  Oct. 15, 2020

Related U.S. Application Data

(60) Division of application No. 15/611,927, filed on Jun. 2, 2017, now Pat. No. 10,729,475, which is a continuation of application No. 13/424,174, filed on Mar. 19, 2012, now Pat. No. 9,687,278.

(60) Provisional application No. 61/454,833, filed on Mar. 21, 2011.

(51) Int. Cl.
  *A61B 17/86* (2006.01)
  *A61B 17/70* (2006.01)
  *A61B 17/74* (2006.01)

(52) U.S. Cl.
  CPC ........ *A61B 17/7064* (2013.01); *A61B 17/742* (2013.01); *A61B 17/866* (2013.01); *A61B 17/8685* (2013.01)

(58) Field of Classification Search
  CPC ....................................... A61B 17/86–17/8695
  See application file for complete search history.

(56) References Cited

U.S. PATENT DOCUMENTS

| | | | |
|---|---|---|---|
| 1,033,447 A | | 7/1912 | Mower |
| 1,434,394 A | * | 11/1922 | Matthes ............... F16B 13/066 411/53 |
| 4,688,561 A | | 8/1987 | Reese |
| 4,790,304 A | * | 12/1988 | Rosenberg ......... A61B 17/7291 606/302 |
| 5,298,254 A | * | 3/1994 | Prewett ................. A61F 2/2846 514/777 |
| 5,370,646 A | * | 12/1994 | Reese ................ A61B 17/8872 411/509 |

(Continued)

FOREIGN PATENT DOCUMENTS

| | | |
|---|---|---|
| EP | 1676538 A1 | 7/2006 |
| EP | 1864616 A1 | 12/2007 |

(Continued)

OTHER PUBLICATIONS

Jun. 27, 2016 Mexican Second Office Action for Application No. MX/A/2013/010671, dated Jun. 27, 2016 the Mexican counterpart of the present application.

(Continued)

*Primary Examiner* — Zade Coley

(74) *Attorney, Agent, or Firm* — BakerHostetler

(57) ABSTRACT

Disclosed is a bone fixation device of the type useful for connecting two or more bones or bone fragments together or connecting soft tissue or tendon to bone. The device comprises an elongate body having a distal anchor thereon. An axially moveable proximal anchor is carried by the proximal end of the fixation device, to accommodate different bone dimensions and permit appropriate tensioning of the fixation device. A sleeve can surround at least a portion of the bone fixation device to promote bone in-growth with or at the bone joint or fracture to facilitate fusion of the bone segment.

19 Claims, 26 Drawing Sheets

(56) References Cited

U.S. PATENT DOCUMENTS

| | | | |
|---|---|---|---|
| 5,423,818 A * | 6/1995 | Van Hoeck | A61B 17/7008 606/278 |
| 5,984,926 A * | 11/1999 | Jones | A61B 17/686 606/76 |
| 6,156,070 A * | 12/2000 | Incavo | A61F 2/30734 623/23.61 |
| 6,511,481 B2 | 1/2003 | Von et al. | |
| 6,650,033 B2 * | 11/2003 | Mehan | C09J 123/0853 313/318.09 |
| 6,692,530 B2 * | 2/2004 | Doubler | A61F 2/36 606/62 |
| 6,887,243 B2 * | 5/2005 | Culbert | A61B 17/8875 606/65 |
| 6,890,333 B2 * | 5/2005 | von Hoffmann | A61B 17/746 606/67 |
| 6,908,465 B2 | 6/2005 | Von et al. | |
| 7,087,087 B2 * | 8/2006 | Boyer,II | A61F 2/4465 623/23.63 |
| 7,166,107 B2 * | 1/2007 | Anderson | A61B 17/7071 606/86 A |
| 8,696,716 B2 * | 4/2014 | Kartalian | A61B 17/68 606/313 |
| 8,734,462 B2 * | 5/2014 | Reiley | A61B 17/8665 606/105 |
| 9,687,278 B2 | 6/2017 | Childs | |
| 2002/0143334 A1 * | 10/2002 | Hoffmann | A61B 17/8625 606/67 |
| 2004/0127906 A1 * | 7/2004 | Culbert | A61B 17/7064 606/279 |
| 2004/0157798 A1 * | 8/2004 | Little | A61K 38/39 514/102 |
| 2004/0199162 A1 * | 10/2004 | von Hoffmann | A61B 17/8625 606/67 |
| 2005/0033289 A1 * | 2/2005 | Warren | A61B 17/68 606/53 |
| 2005/0113919 A1 * | 5/2005 | Cragg | A61F 2/442 623/17.11 |
| 2005/0143734 A1 * | 6/2005 | Cachia | A61B 17/683 606/60 |
| 2005/0251143 A1 * | 11/2005 | Dillard | A61B 17/0401 606/907 |
| 2006/0089642 A1 | 4/2006 | Diaz et al. | |
| 2006/0089646 A1 * | 4/2006 | Bonutti | A61L 27/3834 606/279 |
| 2006/0095040 A1 * | 5/2006 | Schlienger | A61B 17/863 606/313 |
| 2006/0235410 A1 | 10/2006 | Ralph et al. | |
| 2007/0260248 A1 * | 11/2007 | Tipirneni | A61B 17/683 606/65 |
| 2008/0177334 A1 * | 7/2008 | Stinnette | A61B 17/8685 606/301 |
| 2009/0036893 A1 * | 2/2009 | Kartalian | A61B 17/1775 606/301 |
| 2009/0099610 A1 * | 4/2009 | Johnson | A61B 17/844 606/86 R |
| 2010/0331891 A1 * | 12/2010 | Culbert | A61B 17/7064 606/301 |
| 2011/0087296 A1 * | 4/2011 | Reiley | A61B 17/1659 606/301 |
| 2011/0144766 A1 * | 6/2011 | Kale | A61B 17/686 606/300 |
| 2011/0257689 A1 * | 10/2011 | Fiechter | A61B 17/866 606/301 |
| 2011/0269667 A1 * | 11/2011 | Shoseyov | A61K 38/39 530/370 |
| 2011/0288588 A1 * | 11/2011 | Chin | A61B 17/866 606/264 |

FOREIGN PATENT DOCUMENTS

| | | | | |
|---|---|---|---|---|
| WO | 2004/008949 A2 | 1/2004 | | |
| WO | 2006/047363 A1 | 5/2006 | | |
| WO | 2007/048038 A2 | 4/2007 | | |
| WO | 2009/155577 A2 | 12/2009 | | |
| WO | WO-2009155577 A2 * | 12/2009 | | A61B 17/686 |
| WO | 2010/011941 A2 | 1/2010 | | |
| WO | 2010/062971 A1 | 6/2010 | | |
| WO | 2010/135156 A1 | 11/2010 | | |
| WO | 2012/048008 A1 | 4/2012 | | |

OTHER PUBLICATIONS

Notification of Transmittal of the International Search Report and the Written Opinion of the International Searching Authority or the Declaration, dated Jun. 19, 2012, PCT/US2012/029707.

Sep. 24, 2013 International Preliminary Report on Patentability (and Written Opinion) for PCT Application No. PCT/US2012/029707, the PCT counterpart of the present application.

Sep. 3, 2015 Mexican Office Action Application No. 2015/37664, the Mexican counterpart of the present application.

* cited by examiner

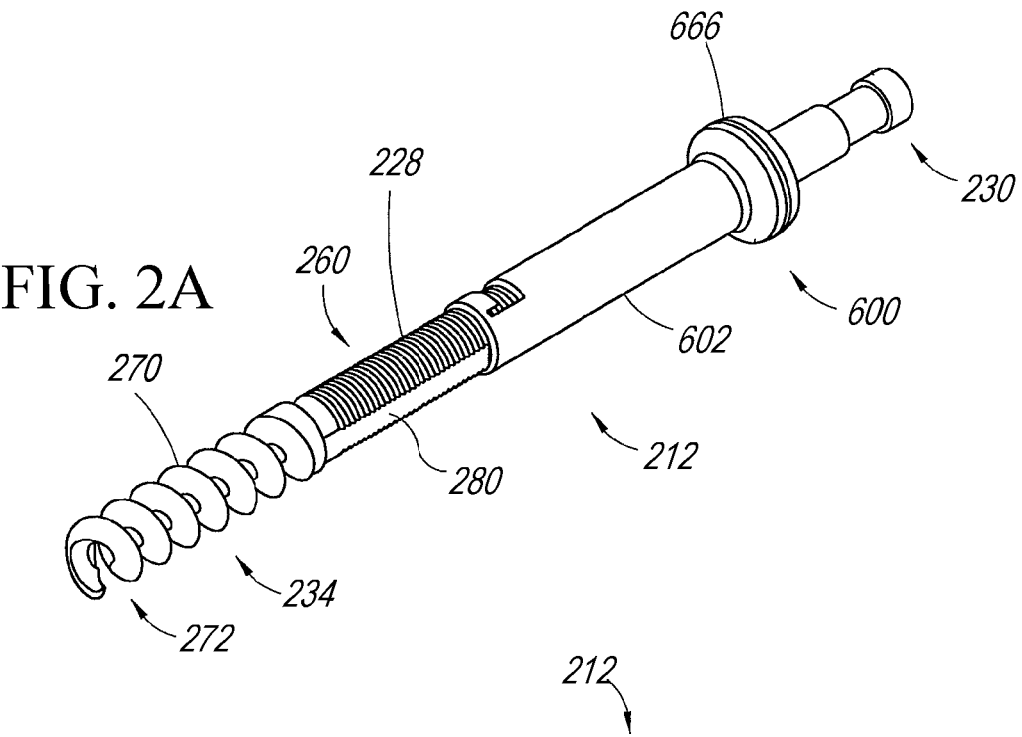
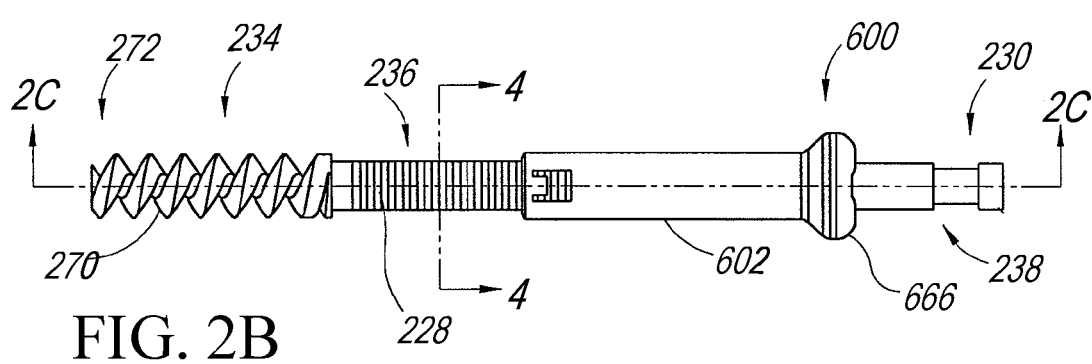
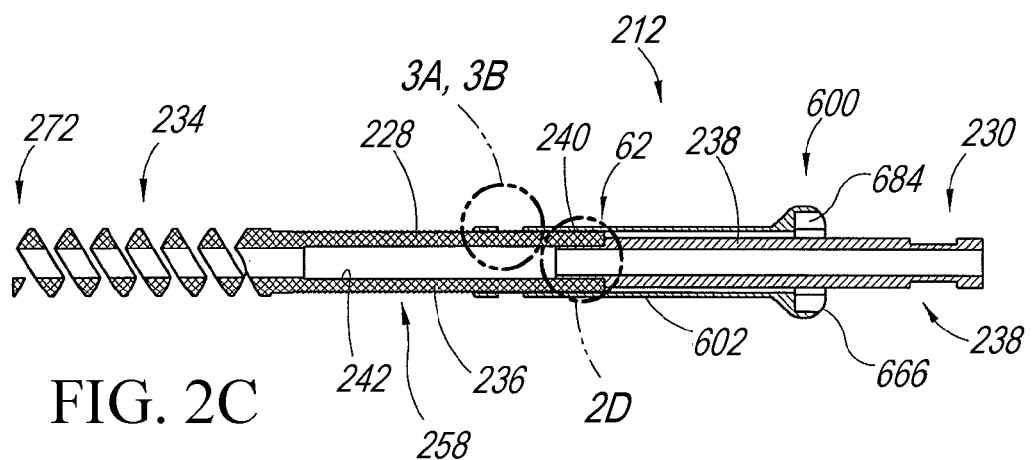

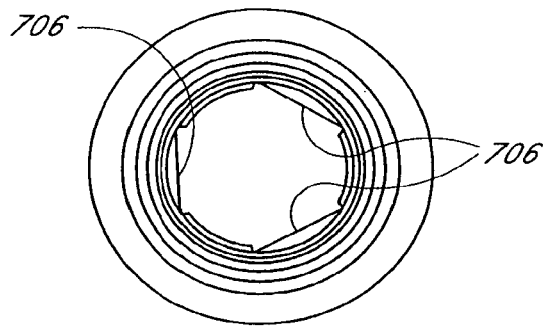
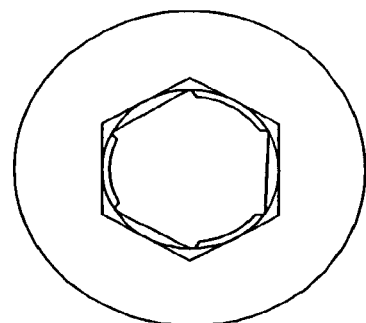
FIG. 5D  FIG. 5E
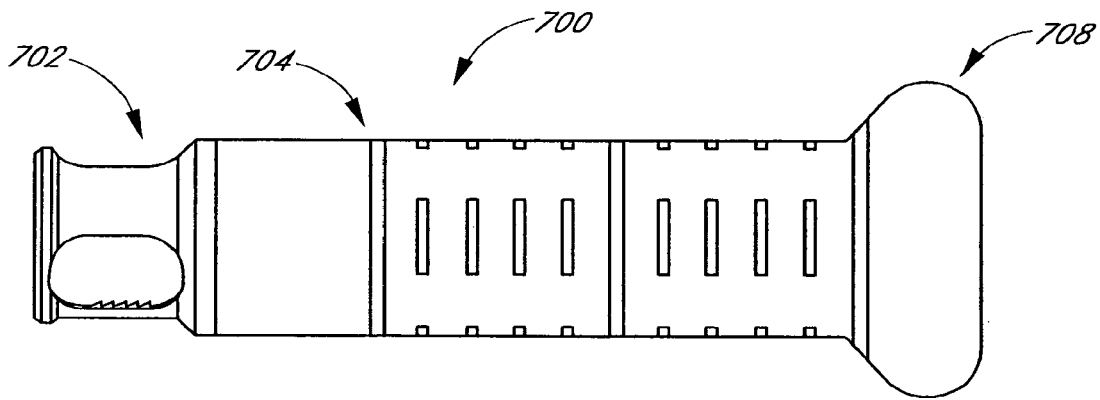
FIG. 5B
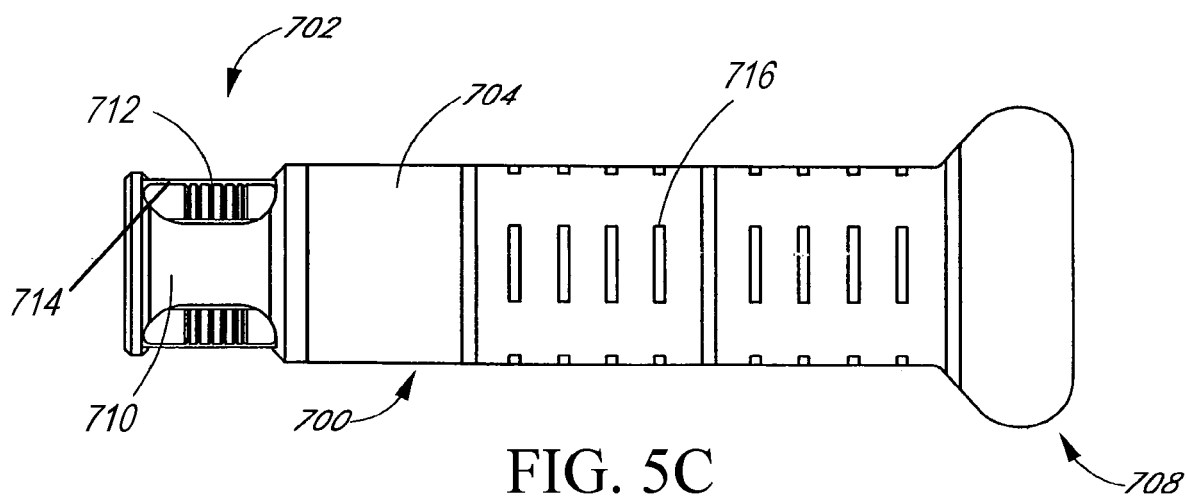
FIG. 5C

SLEEVE FOR BONE FIXATION DEVICE

CROSS-REFERENCE TO RELATED APPLICATIONS

This application is a divisional application of U.S. patent application Ser. No. 15/611,927 filed Jun. 2, 2017, which is a continuation application of U.S. patent application Ser. No. 13/424,174, filed Mar. 19, 2012, which claims a priority benefit to U.S. Provisional Application No. 61/454,833, filed Mar. 21, 2011, the disclosures of each of which are hereby incorporated by reference as if set forth in their entirety herein.

BACKGROUND OF THE INVENTION

Field of the Invention

The present invention relates to medical devices, and, more particularly, to bone fixation devices.

Description of the Related Art

Bones which have been fractured, either by accident or severed by surgical procedure, must be kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body can then be kept at a minimum, such as by application of a cast, brace, splint, or other conventional technique, in order to promote healing and avoid mechanical stresses that can cause the bone parts to separate during bodily activity.

The surgical procedure of attaching two or more parts of a bone with a pin-like device requires an incision into the tissue surrounding the bone and the drilling of a hole through the bone parts to be joined. Due to the significant variation in bone size, configuration, and load requirements, a wide variety of bone fixation devices have been developed in the prior art. In general, the current standard of care relies upon a variety of metal wires, screws, and clamps to stabilize the bone fragments during the healing process. Following a sufficient bone healing period of time, the percutaneous access site or other site can require re-opening to permit removal of the bone fixation device.

Furthermore, a variety of methods have been developed to treat displaced or fractured vertebra and to fix them within the vertebral column. Such methods typically include various fixation systems that are used for the stabilization of fractures and/or fusions of various portions of the spine. These fixation systems may include a variety of longitudinal elements such as rods or plates which span two or more vertebra and are affixed to the vertebra by various fixation elements such as wires, staples, and screws (often inserted through the pedicles of the vertebra). These systems may be affixed to either the posterior or the anterior side of the spine. In other applications, one or more bone screws may be inserted through adjacent vertebrae to provide stabilization.

The internal fixation techniques commonly followed today frequently rely upon the use of screws, plates, Kirschner wires (K-wires), intramedullary pins, wiring and combinations of the foregoing. The particular device or combination of devices is selected to achieve the best anatomic and functional condition of the traumatized bone with the simplest operative procedure and with a minimal use of foreign-implanted stabilizing material. A variety of alternate bone fixation devices are also known in the art, such as, for example, those disclosed in U.S. Pat. No. 4,688,561 to Reese, U.S. Pat. No. 4,790,304 to Rosenberg, and U.S. Pat. No. 5,370,646 to Reese, et al.

A variety of elongated implants (nail, screw, pin, etc.) have been developed, which are adapted to be positioned along the longitudinal axis of the femoral neck with a leading distal end portion in the femoral head so as to stabilize a fracture of the femoral neck. The elongated implant can be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Bone fasteners can also be used for the stabilization of fractures and/or fusion of various portions of the spine. Such fasteners are often inserted through the pedicles of the vertebra and can be used in combination with a variety of longitudinal elements such as rods or plates which span two or more vertebra. These systems can be affixed to either the posterior or the anterior side of the spine.

Notwithstanding the variety of bone fasteners that have been developed in the prior art, there remains a need for a bone fixation device that effectively integrates with the bone to secure a fracture, secure soft tissue or tendon to the bone and/or provide stability between bones (e.g., vertebrae).

SUMMARY OF THE INVENTION

There is provided in accordance with some embodiments of the present invention, a fixation device for securing a first bone fragment to a second bone fragment or a first bone to a second bone. Alternatively, the fixation device can be used to secure soft tissue to a bone. The fixation device can comprise a sleeve disposed around the outer surface that promotes integration of the fixation device with bone material.

In some embodiments, an orthopedic fixation device comprises an elongate body having a proximal end with a proximal anchor and a distal end with a distal anchor. A sleeve covers at least a portion of the fixation device. The sleeve comprises a material configured promote fusion within a joint or fracture.

One embodiment comprises a sleeve for use with an orthopedic fixation device. The sleeve comprising a tubular body with an inner diameter that is generally the same as the outer diameter of the fixation device. The sleeve is configured to promote fusion across a bone fracture or joint.

Another embodiment comprises a method of providing bone fixation. The method can include advancing a fixation device that comprises a body having a first portion that forms a bone anchor and a second portion that forms a proximal end into a first structure of a bone structure, securing the first structure to a second structure by advancing a proximal anchor against the second structure; and placing a sleeve formed substantially of allograft and carried by the fixation device across a juncture between the first structure and the second structure.

Another embodiment comprises a method of providing bone fixation. The method can include forming a hole extending across a juncture between the first structure and the second structure fixation and advancing a sleeve formed substantially of bone allograft into the hole such that the sleeve spans the juncture between the first structure and the second structure.

Further features and advantages of the present application will become apparent to those of skill in the art in view of the detailed description of preferred embodiments which follows, when considered together with the attached claims and drawings.

BRIEF DESCRIPTION OF THE DRAWINGS

FIG. 2A is a side perspective view of a fixation device similar to that of FIG. 1.

FIG. 2B is a side elevational view of the fixation device of FIG. 2A.

FIG. 2C is a cross-sectional view taken through line 4-4 of FIG. 2B.

FIGS. 5A-F are perspective, side, top, bottom and cross-sectional views of an embodiment of a proximal anchor.

DETAILED DESCRIPTION OF THE PREFERRED EMBODIMENTS

As will be described below, in certain embodiments, sleeves or similar structures that fit over the collar or shaft of a fixation device can so as to cross a bone joint or fracture site to promote bone in-growth and fusion within the bone joint or at the fracture site. The sleeves can be made of a biocompatible material, such as allograft (e.g., cortical bone, cancellous bone, demineralized bone matrix (DBM) or bone morphogenic protein (BMP)), that promotes bone in-growth and fusion within and/or across the joint (or facture). The embodiments of fixation devices described herein will be disclosed primarily in the context of a spinal fixation procedure and fusion across a facet joint. However, the methods and structures disclosed herein are intended for application in any of a variety medical applications, as will be apparent to those of skill in the art in view of the disclosure herein.

As noted above, the bone fixation devices described herein can be used in a variety of techniques to stabilize the spine. For example, the bone fixation devices can be used as pedicle or facet screws that can be unilaterally or bilaterally symmetrically mounted on adjacent or non-adjacent vertebrae and used in combination one or more linkage rods or plates to facilitate fusion across the facet joint and between one or more vertebrae. The bone fixation devices disclosed herein can also be used as a fixation screw to secure two adjacent vertebra to each other in a trans-laminar, trans-facet or facet-pedicle (e.g., the Boucher technique) applications. One of skill of the art will also recognize that the bone fixation devices disclosed herein can be used for posterior stability after laminectomy, artificial disc replacement, repairing odontoid fractures and other fractures of the spine, and other applications for providing temporary or permanent stability in the spinal column.

In other embodiments, the bone fixation devices can be in a wide variety of fractures and such as, for example, osteotomies in the hand, foot, and tarsal bones such as the calcaneus and talus. In other embodiments, fibular and tibial malleoli, pilon fractures and other fractures of the bones of the leg can be fixated and stabilized with one or more of the embodiments described herein. In yet other embodiments, the fixation device can also be used in the context of fractures of the proximal femur.

Figure 1:
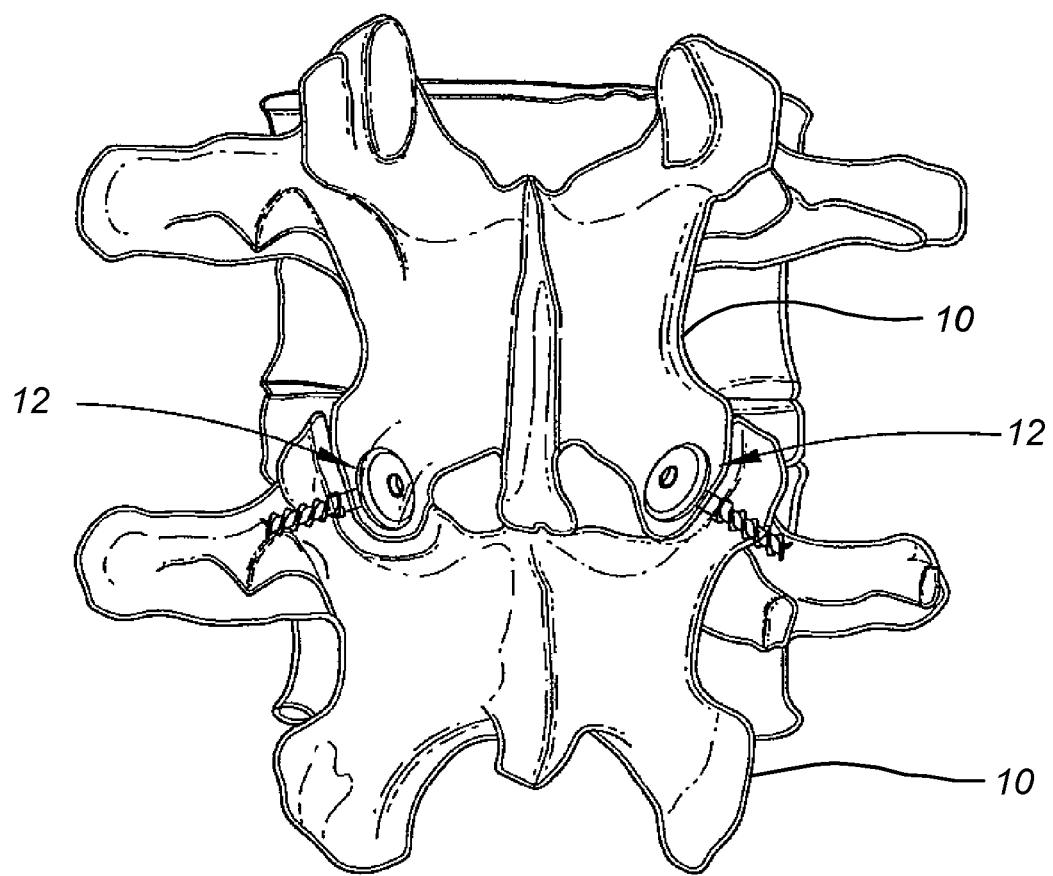
FIG. 1 is a posterior elevational view of a portion of a vertebra having an embodiment of a fixation device implanted therein.

Referring to FIG. 1, there is illustrated a side elevational view of an embodiment of a bone fixation device 12 positioned within adjacent vertabrae 10. As will be explained in more detail below, the fixation device 12 may be used in a variety of techniques to stabilize the spine. For example, in the illustrated embodiment, the fixation devices 12 can be used as pedicle or facet screws that may be unilaterally or bilaterally symmetrically mounted on adjacent or non-adjacent vertebrae and used in combination one or more linkage rods or plates to facilitate fusion of one or more vertebrae. The fixation devices 12 disclosed herein may also be used as a fixation screw to secure two adjacent vertebra to each other in a trans-laminar, trans-facet or facet-pedicle (e.g., the Boucher technique) applications. One of skill of the art will also recognize that the bone fixation devices disclosed herein may be used for posterior stability after laminectomy, artificial disc replacement, repairing odontoid fractures and other fractures of the spine, and other applications for providing temporary or permanent stability in the spinal column.

Fixation Device

Figure 2D:
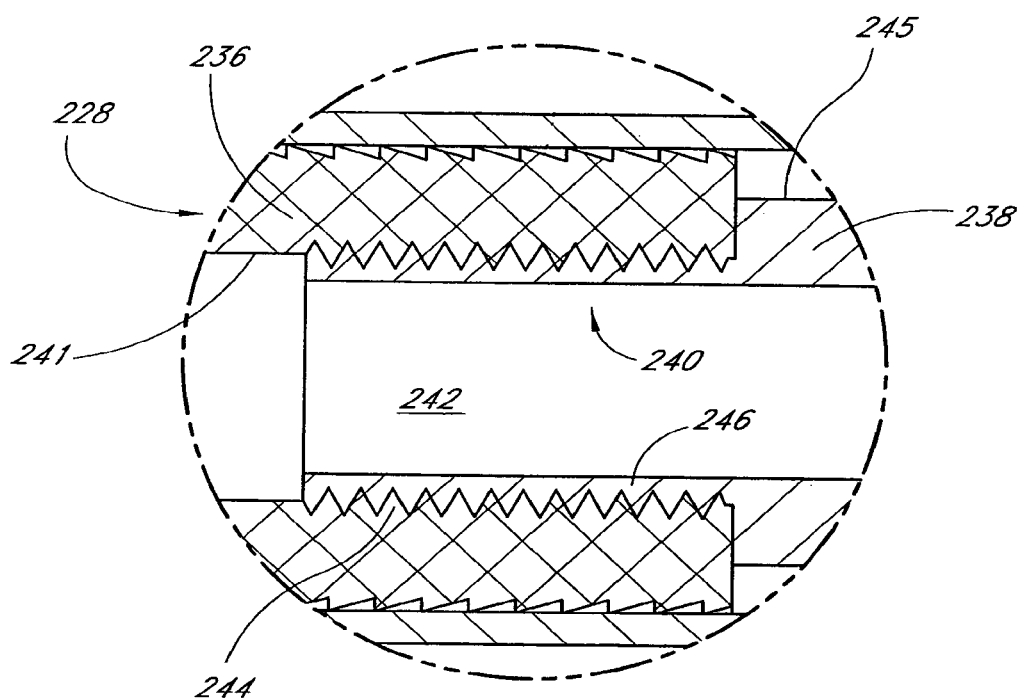
FIG. 2D is an enlarged view of portion 2D of FIG. 2C.

FIGS. 2A-D illustrate an embodiment of a fixation device 212 having a body 228 and a proximal anchor 600. In the illustrated embodiment, the body 228 comprises a first portion 236 and a second portion 238 that are coupled together at a junction 240 (FIG. 2D). The first portion 236 can carry the distal anchor 234 while the second portion 238 forms the proximal end 230 of the body 228. The first and second portions 236, 238 are preferably detachably coupled to each other at the junction 240. In the illustrated embodiment, the first and second portions 236, 238 are detachably coupled to each other via interlocking threads. Specifically, as best seen in FIG. 2D, the body 228 can include an inner surface 241, which defines a central lumen 242 that preferably extends from the proximal end 230 to the distal end 232 throughout the body 228. At the proximal end of the first portion 236, the inner surface 241 can include a first threaded portion 244. The first threaded portion 244 can be configured to mate with a second threaded portion 246, which is located on the outer surface 245 of the second portion 238. The interlocking annular threads of the first and second threaded portions 244, 246 can enable the first and second portions 236, 238 to be detachably coupled to each other. In some embodiments, the orientation of the first and second threaded portions 244, 246 can be reversed. That is, the first threaded portion 244 can be located on the outer surface of the first portion 236 and the second threaded portion 246 can be located on the inner surface 241 at the distal end of the second portion 238. Any of a variety of other releasable complementary engagement structures can also be used, to allow removal of second portion 238 following implantation, as is discussed below.

The second portion 238 can comprise any of a variety of tensioning elements for permitting proximal tension to be placed on the distal anchor 234 while the proximal anchor 600 is advanced distally to compress the fracture. For example, any of a variety of tubes or wires can be removably attached to the first portion 236 and extend proximally to the proximal handpiece. In one such arrangement, the first portion 236 can include a releasable connector in the form of a latching element, such as an eye or hook. The second portion 238 can include a complementary releasable connector (e.g., a complementary hook or eye) for engaging the first portion 236. In this manner, the second portion 238 can be detachably coupled to the first portion 236 such that proximal traction can be applied to the first portion 236 through the second portion, as will be explained below. Alternatively, the second portion 238 can be provided with an eye or hook, or transverse bar, around which or through which a suture or wire can be advanced, both ends of which are retained at the proximal end of the device. Following proximal tension on the tensioning element during the compression step, one end of the suture or wire is released, and the other end can be pulled free of the device. Alternate releasable proximal tensioning structures can be devised by those of skill in the art in view of the disclosure herein.

With continued reference to FIG. 2A, the proximal anchor 600 can comprise a housing 602 such as a tubular body, for coaxial movement along the body 228. At the proximal end of the housing 602 can be a flange 666, such as an enlarged portion that is configured to contact the surface of a bone. As will be explained in more detail below, in certain embodiments, the housing 602 may have diameter sized to fit through an opening formed in fixation bar or plate.

As will be explained below, the flange 666 can be configured to sit against the outer surface of a vertebra, a fixation plate, a fixation rod and/or a washer. The flange 666 is preferably an annular flange, to optimize the footprint or contact surface area between the flange 666 and the bone or other device. Circular or polygonal shaped flanges for use in spinal fixation will generally have a diameter of at least about 3 mm greater than the adjacent body 228 and often within the range of from about 2 mm to about 30 mm or more greater than the adjacent body 228.

With continued reference to FIGS. 2A-2D, the proximal end 230 of the body 228 can be provided with a rotational coupling 270, for allowing the second portion 238 of the body 228 to be rotationally coupled to a rotation device. The proximal end 230 of the body 228 can be desirably rotated to accomplish some discrete functions. In some embodiments, the proximal end 230 can be rotated to remove the second portion 238 of the body 228 following tensioning of the device across a fracture or to anchor an attachment to the bone. Rotation of the rotational coupling 270 can also be utilized to rotationally drive the distal anchor into the bone. Any of a variety of rotation devices can be utilized, such as electric drills or hand tools, which allow the clinician to manually rotate the proximal end 230 of the body. Thus, the rotational coupling 270 can have any of a variety of cross sectional configurations, such as one or more flats or splines.

With particular reference to FIG. 2A, the fixation device can include an antirotation lock between the first portion 236 of the body 228 and the proximal anchor 600. In the illustrated embodiment, the first portion 236 includes a pair of flat sides 280, which interact with corresponding flat structures 282 in the proximal anchor 600. One, three or more axially extending flats can also be used. As such, rotation of the proximal anchor 600 can be transmitted to the first portion 236 and the distal anchor 234 of the body 228. Of course, those of skill in the art will recognize various other types of splines or other interfit structures can be used to prevent relative rotation of the proximal anchor and the first portion 236 of the body 228. For example, in some embodiments, the first portion 236 can include three flat sides, which interact with corresponding flat structures on the proximal anchor.

Figure 5A:
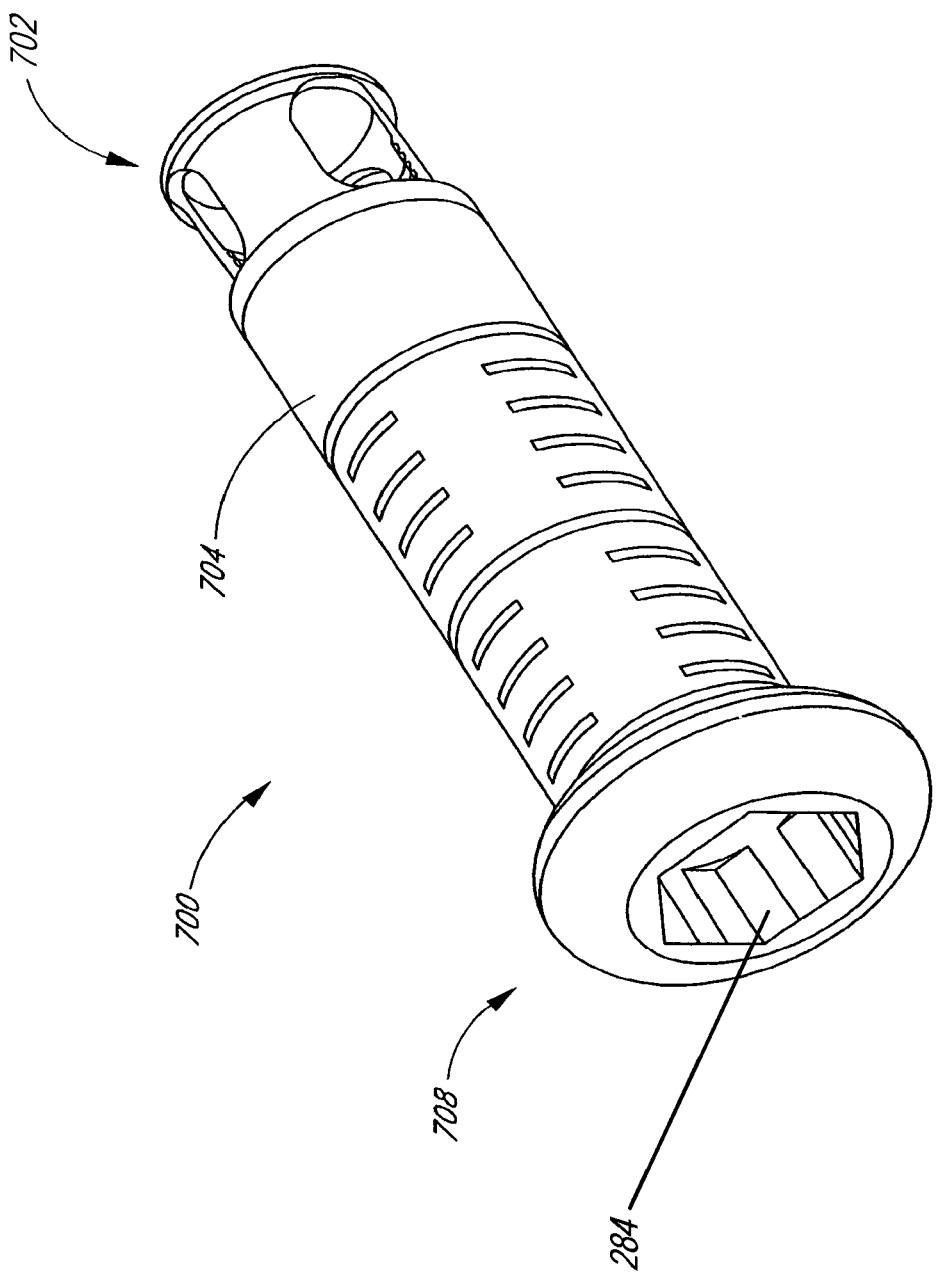
Figure 5F:
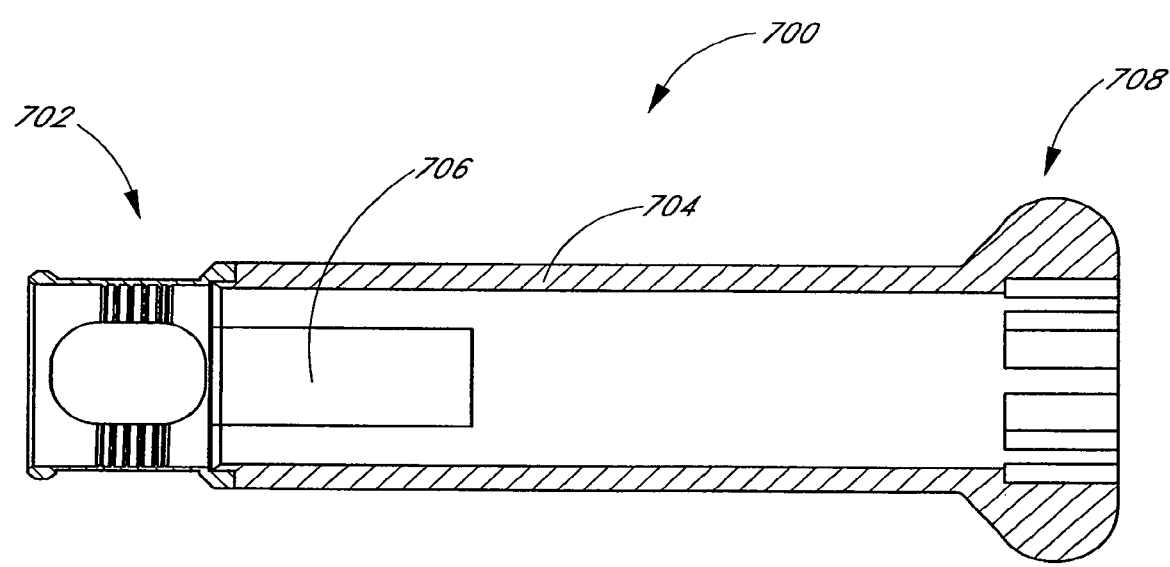

To rotate the proximal anchor 600, the flange 708 is preferably provided with a gripping structure to permit an insertion tool to rotate the flange 708. Any of a variety of gripping structures can be provided, such as one or more slots, flats, bores or the like. In some embodiments, the flange 708 can be provided with a polygonal, and, in particular, a pentagonal or hexagonal recess 284, as illustrated in FIG. 5A.

Tensioning and release of the proximal anchor 600 can be accomplished in a variety of ways, depending upon the intended installation and removal technique. For example, a simple threaded relationship between the proximal anchor 600 and body 228 enables the proximal anchor 600 to be rotationally tightened as well as removed. However, depending upon the axial length of the threaded portion on the body 228, an undesirably large amount of time can be required to rotate the proximal anchor 600 into place. For this purpose, the locking structures on the proximal anchor 600 can be adapted to elastically deform or otherwise permit the proximal anchor 600 to be distally advanced along the body 228 without rotation, during the tensioning step. The proximal anchor 600 can be removed by rotation as has been discussed. In addition, any of a variety of quick release and quick engagement structures can be utilized. For example, the threads or other retention structures surrounding the body 228 can be interrupted by two or more opposing flats 280. Two or more corresponding flats are provided on the interior of the housing 602. By proper rotational alignment of the housing 602 with respect to the body 228, the housing 602 can be easily distally advanced along the body 228 and then locked to the body 228 such as by a 90° or other partial rotation of the housing 602 with respect to the body 228. Other rapid release and rapid engagement structures can also be devised.

Figure 3A:
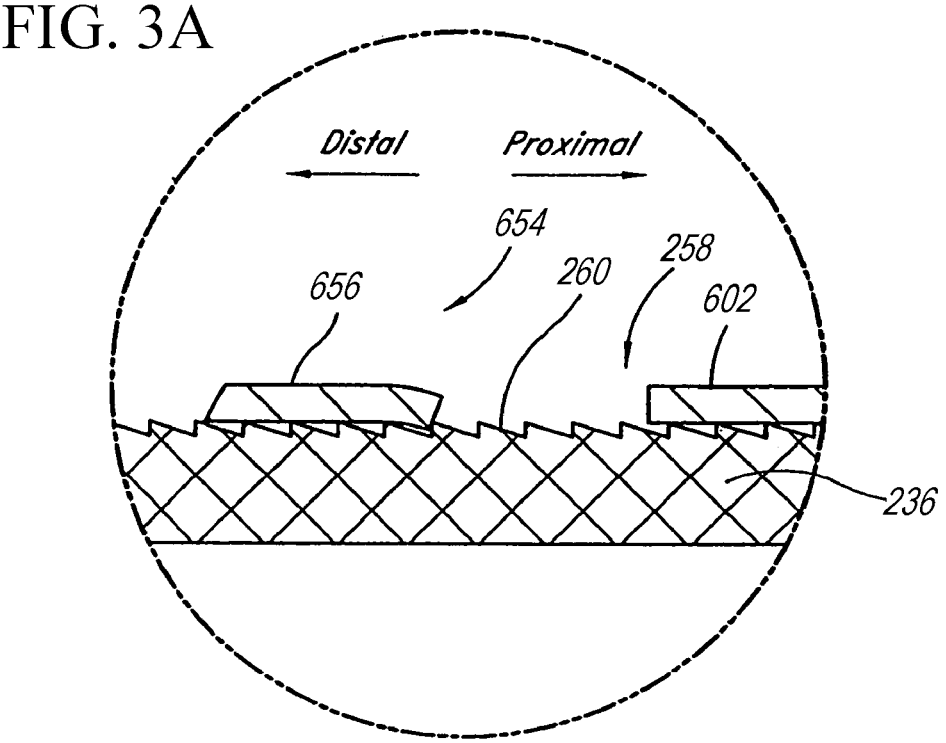
FIG. 3A is an enlarged view of portion 3A of FIG. 2C with the fixation device in a first position.
Figure 3B:
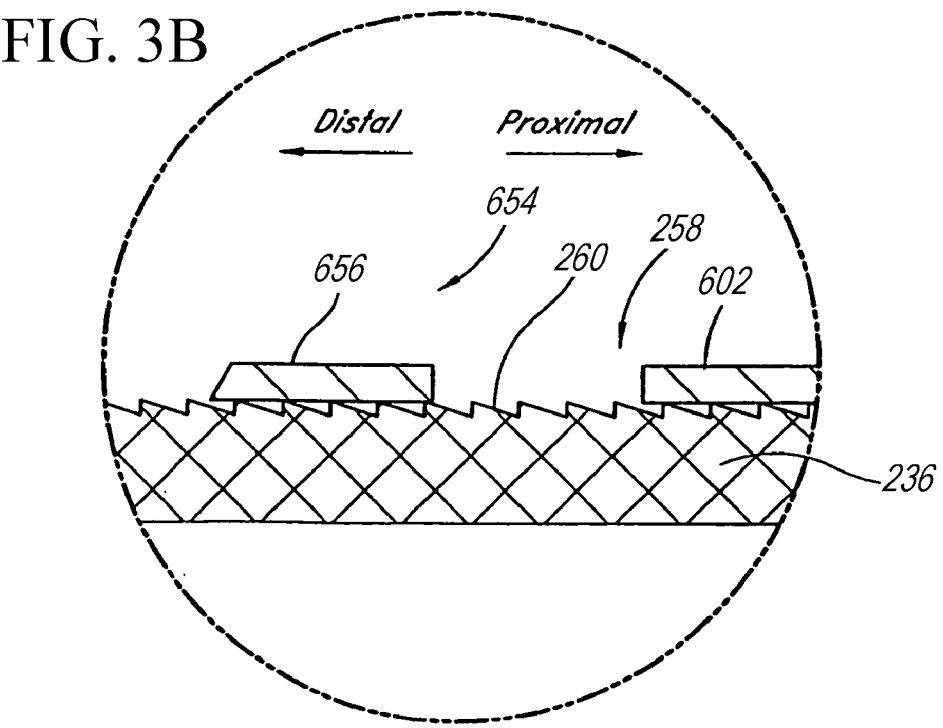
FIG. 3B is an enlarged view of portion 3B of FIG. 2C with the fixation device in a second position.

In a final position, the distal end of the housing 602 preferably extends distally past the junction 240 between the first portion 236 and the second portion 238. As illustrated in FIGS. 3A and 3B, the housing 602 can be provided with one or more surface structures 654, such as a radially inwardly projecting flange 656, for cooperating with complementary surface structures 258 on the first portion 236 of the body 228. In the illustrated embodiment, the complimentary surface structures 258 comprise a series of annular ridges or grooves 260. The surface structures 654 and complementary surface structures 258 permit distal axial travel of the proximal anchor 600 with respect to the body 228, but resist proximal travel of the proximal anchor 600 with respect to the body 228.

For example, as best seen in FIG. 3A, the proximal end of the flange 656 can be biased towards the longitudinal axis of the body 228. When the proximal anchor 600 is urged proximally with respect to the body 228, the flange 656 can engage the grooves or ridges 260 of the complementary surface structures 258. This prevents proximal movement of the proximal anchor 600 with respect to the body 228. In contrast, as best seen in FIG. 3B, when the proximal anchor 600 is moved distally with respect to the body 228, the flange 656 can bend outwardly away from the body 228 and the ridges 260 so as to allow the proximal anchor 600 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In some embodiments, opposing screw threads can be dimensioned to function as a ratchet.

Surface structures 258 can be spaced axially apart along the body 228, between a proximal limit and a distal limit. The axial distance between proximal limit and distal limit is related to the desired axial working range of the proximal anchor 600, and thus the range of functional sizes of the fixation device 212. The fixation device 212 of the exemplary embodiment can provide compression between the distal anchor 234 and the proximal anchor 600 throughout a range of motion following the placement of the distal anchor in a vertebra. That is, the distal anchor 234 may be positioned within the cancellous and/or distal cortical bone of a vertebra, and the proximal anchor 600 may be distally advanced with respect to the distal anchor 234 throughout a range to provide compression without needing to relocate the distal anchor 234 and without needing to initially locate the distal anchor 234 in a precise position with respect to the proximal side of the bone or another vertebra. Providing a working range throughout which tensioning of the proximal anchor 600 is independent from setting of the distal anchor 234 can allow a single device to be useful for a wide variety of spinal fixation procedures, as well as eliminate the need for accurate device measurement. In addition, this arrangement can allow the clinician to adjust the compression force during the procedure without adjusting the position of the distal anchor 234. In this manner, the clinician can focus on positioning the distal anchor sufficiently within the vertebra to avoid or reduce the potential for distal migration out of the vertebra, which may damage the particularly delicate tissue, blood vessels, nerves and/or spinal cord surrounding or within the spinal column.

In many applications, the working range can be at least about 10% of the overall length of the device, and may be as much as 20% or 50% or more of the overall device length. In the context of a spinal application, working ranges of up to about 10 mm or more can be provided, since estimates within that range can normally be readily accomplished within the clinical setting. The embodiments disclosed herein can be scaled to have a greater or a lesser working range, as will be apparent to those of skill in the art in view of the disclosure herein.

Figure 4:
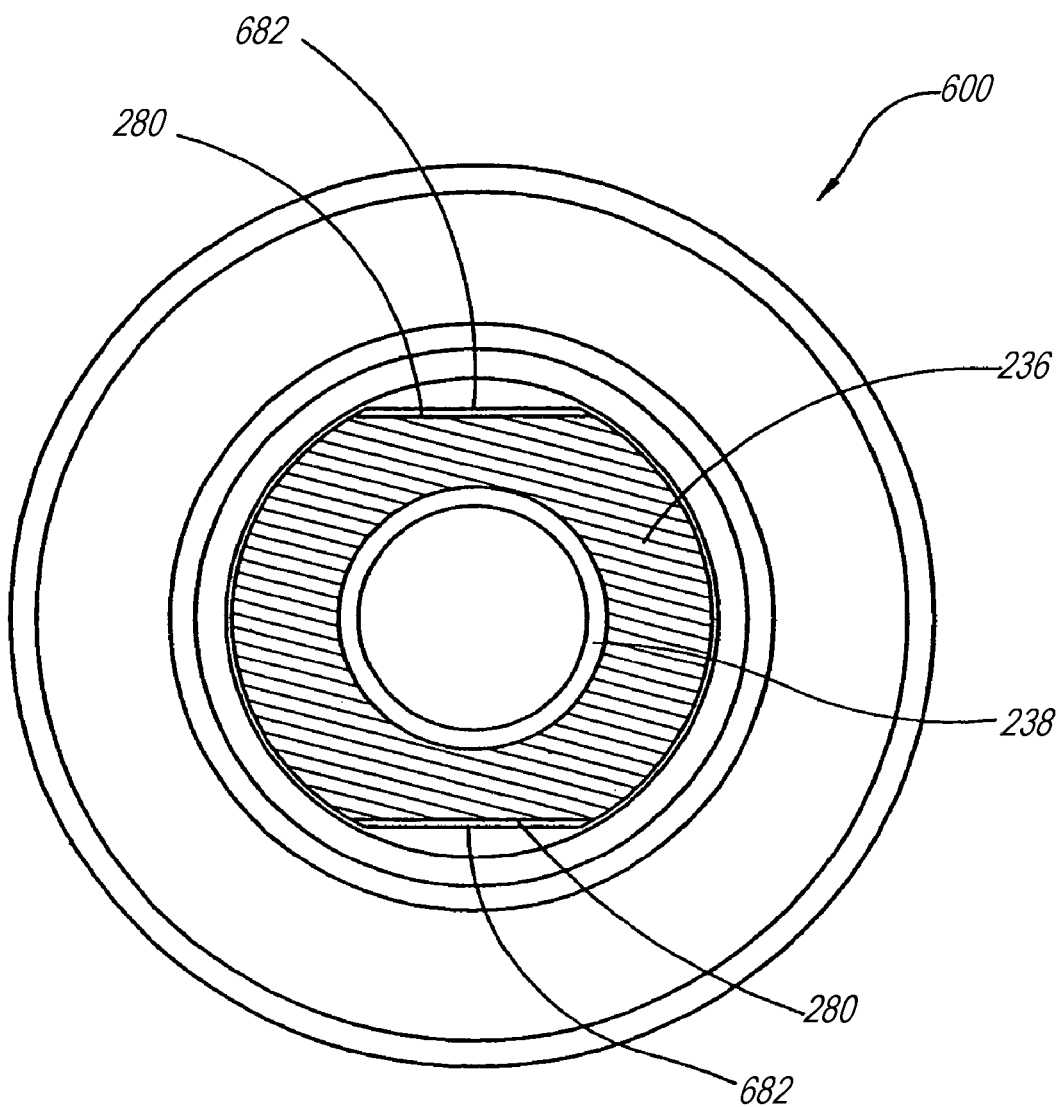
FIG. 4 is a cross-sectional view taken through line 4-4 of FIG. 2B.

With particular reference to FIGS. 2 and 4, the fixation device may include an antirotation feature between the first portion 236 of the body 228 and the proximal anchor 600. In the illustrated embodiment, the first portion 236 includes a pair of flat sides 280, which interact with corresponding flat structures 682 in the proximal anchor 600. One or three or more axially extending flats may also be used. Rotation of the proximal anchor 600 can be transmitted to the first portion 236 and distal anchor 234 of the body 228. Of course, those of skill in the art will recognize various other types of splines or other interfit structures can be used to prevent relative rotation of the proximal anchor and the first portion 236 of the body 228.

To rotate the proximal anchor 600, the flange 666 is preferably provided with a gripping structure to permit an insertion tool to rotate the flange 666. Any of a variety of gripping structures may be provided, such as one or more slots, flats, bores or the like. In some embodiments, the flange 666 can be provided with a polygonal, and, in particular, a pentagonal or hexagonal recess 684.

In a modified embodiment, the housing 602 of the proximal anchor 600 can include one or more barbs that extend radially outwardly from the tubular housing 602. Such barbs provide for self tightening after the device has been implanted in the patient as described in a U.S. Pat. No. 6,908,465, issued Jun. 21, 2005, which is incorporated by reference in its entirety herein. The barbs may be radially symmetrically distributed about the longitudinal axis of the housing 602. Each barb can be provided with a transverse engagement surface, for anchoring the proximal anchor 600 in the bone. The transverse engagement surface may lie on a plane which is transverse to the longitudinal axis of the housing 602 or may be inclined with respect to the longitudinal axis of the proximal anchor 600. In either arrangement, the transverse engagement surface generally faces the contacting surface of the flange. As such, the transverse engagement surface inhibits proximal movement of the proximal anchor with respect to the bone.

FIGS. 5A-5F illustrate another embodiment of a proximal anchor 700. The proximal anchor 700 can include a tubular housing 702. In the illustrated embodiment, the tubular housing 702 is attached to, coupled to, or integrally formed (partially or wholly) with a secondary tubular housing 704, which includes one or more anti-rotational features 706 (e.g., flat sides) for engaging corresponding anti-rotational features formed on the first portion 236. A flange or collar 708 can be attached, coupled or integrally formed with the proximal end of the secondary tubular housing. The illustrated embodiment also advantageously includes visual indicia 716 (e.g., marks, grooves, ridges etc.) on the tubular housing 704 for indicating the depth of the proximal anchor 700 within the bone.

As illustrated in FIG. 5C, the tubular housing 702 can have bridges 710 with teeth or flanges 712 that can be configured such that the proximal anchor 700 can be distally advanced and/or removed with rotation. The teeth or grooves 112 can be configured to engage complementary surfaces structures on the body 228 (see FIG. 2A). One or more slots or openings 714 can be formed in the tubular housing 702. The proximal anchor 700 can be pushed towards the distal end of the body 228 and the teeth 712 can slide along the and over the complementary surface structures 258 on the body 228. In the illustrated embodiment, the bridge 710 can flex slightly away from the body 228 to allow such movement. The number and shape of the openings 714 and bridges 710 can be varied depending of the desired flexing of the bridges 710 when the proximal anchor 700 is moved distally over the body and the desired retention force of the distal anchor 700 when appropriately tensioned. In some embodiments, the teeth on the proximal anchor 700 and the grooves on the body 228 can be configured such that the proximal anchor 700 can be rotated or threaded onto the first portion 236 in the distal direction and/or so that that the proximal anchor 700 can be removed by rotation.

FIGS. 6A-6D illustrate another embodiment of a proximal anchor 800. In the illustrated embodiment, the proximal anchor 800 includes a recess 839 configured to receive a split ring 434. As will be explained in detail below, the proximal anchor 800 can include an anti-rotation feature to limit or prevent rotation of the ring 434 within the proximal anchor 800. In light of the disclosure herein, those of skill in the art will recognize various different configurations for limiting the rotation of the ring 434.

In the illustrated embodiment, the proximal anchor 800 has a tubular housing 804 that can engage with a body 228 or a first portion 236 of a body 228 as described above. With reference to FIGS. 6B and 6D, the tubular housing 804 can comprise one or more anti-rotational features 806 in the form of a plurality of flat sides that are configured to mate corresponding anti-rotational features 280 or flat sides of the body 228 of the fixation device. As shown in FIG. 6D, in the illustrated embodiment, the body 228 can have three flat sides 280. Disposed between the flat sides 280 are the portions of the body 228 which include the complementary locking structures such as threads or ratchet like structures as described above. The complementary locking structures can interact with the ring 434 as described above to resist proximal movement of the anchor 800 under normal use conditions while permitting distal movement of the anchor 800 over the body 228.

As mentioned above, the ring 434 can be positioned within the recess 839. In the illustrated embodiment, the recess 839 and ring 434 are positioned near to and proximal of the anti-rotational features 806. However, the ring 434 can be located at any suitable position along the tubular housing 804 such that the ring 434 can interact with the retention features of the body During operation, the ring 434 can rotate to a position such that the gap 431 between the ends 433a, 433b of the ring 434 lies above the complementary retention structures on the body 228. When the ring 434 is in this position, there is a reduced contact area between the split ring 434 and the complementary retention structures thereby reducing the locking strength between the proximal anchor 800 and the body 228. In the illustrated embodiment, for example, the locking strength can be reduced by about ⅓ when the gap 431 is over the complementary retention structures between flat sides 280. As such, it is advantageous to position the gap 431 on the flat sides 280 of the body 228 that do not include complementary retention structures.

Figure 6A:
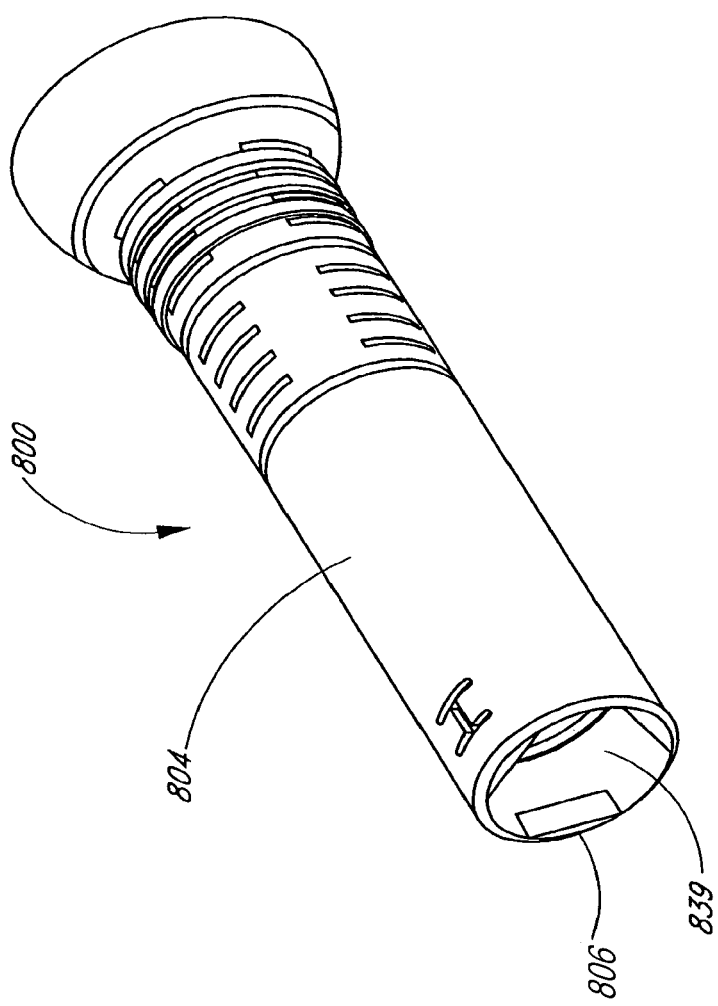
FIG. 6A is a perspective view of another embodiment of a proximal anchor.
Figure 6C:
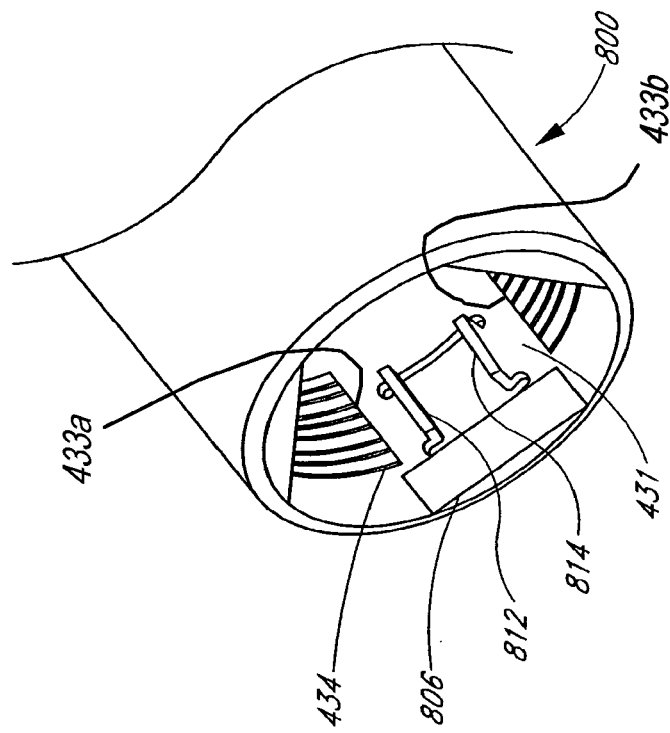
FIGS. 6B and 6C are enlarged views of a portion of an embodiment of a proximal anchor.
Figure 6B:
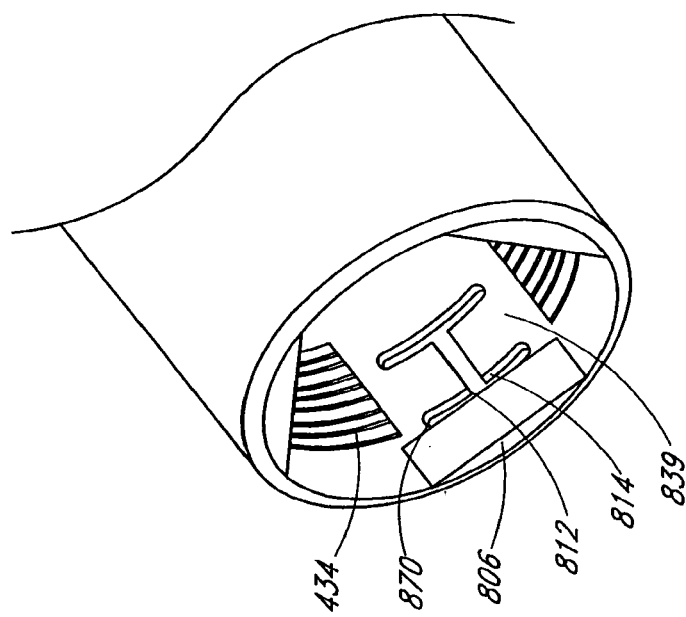
Figure 6D:
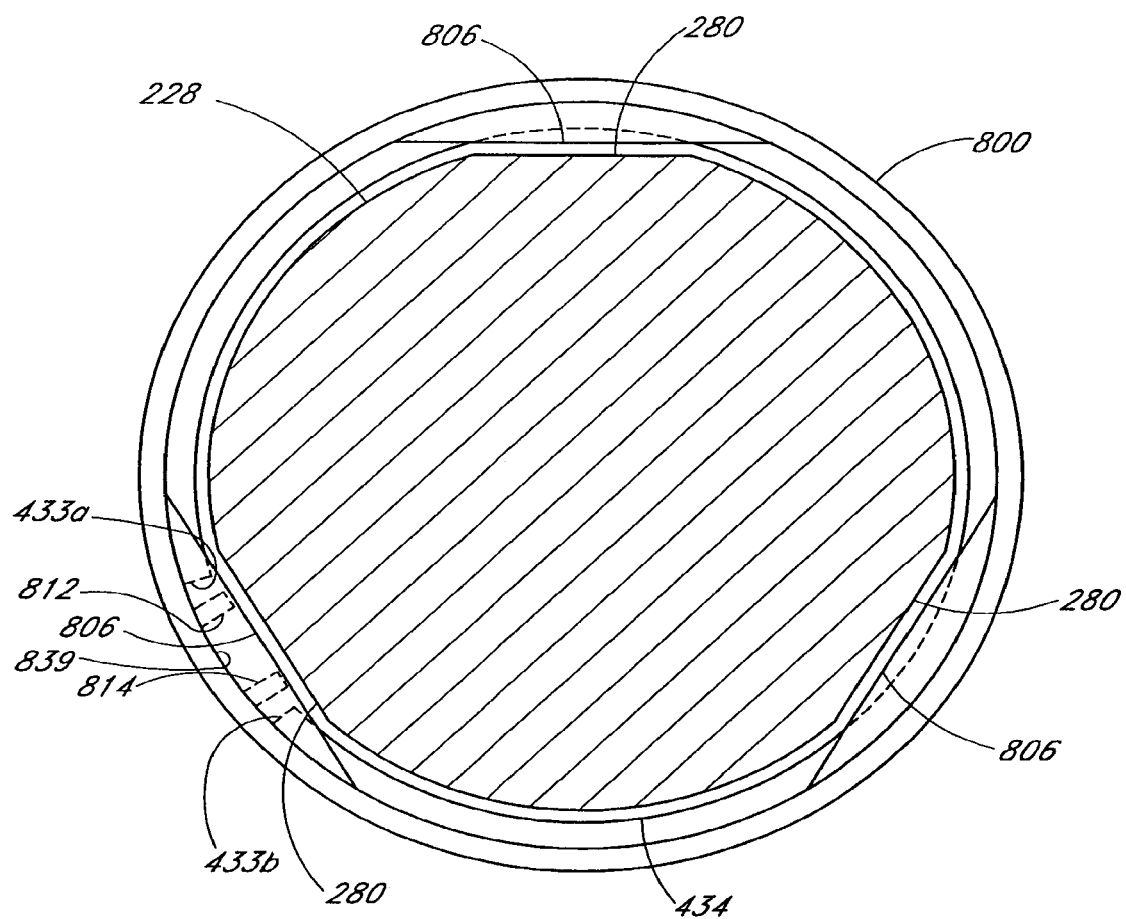
FIG. 6D is a front view of the proximal anchor of FIG. 6A.

To achieve this goal, the housing 804 can include a pair of tabs 812, 814 that extend radially inward from the interior of the proximal anchor 800, as illustrated in FIG. 6C. The tabs 812, 814 are configured to limit or prevent rotational movement of the ring 434 relative to the housing 804 of the anchor 800. In this manner, the gap 431 of the ring 434 can be positioned over the flattened sides 280 of the body 228.

In the illustrated embodiment, the tabs 812, 814 have a generally rectangular shape and have a generally uniform thickness. However, it is contemplated that the tabs 812, 814 can be square, curved, or any other suitable shape for engaging with the ring 434 as described herein.

In the illustrated embodiment, the tabs 812, 814 are formed by making an H-shaped cut 870 in the tubular housing 800 and bending the tabs 812, 814 inwardly as shown in FIG. 6D. As illustrated in FIG. 6D, the tabs 812, 814 (illustrated in phantom) are interposed between the edges 433a, 433b of the ring 434. The edges 433a, 433b of the ring 434 can contact the tabs to limit the rotational movement of the ring 434. Those skilled in the art will recognize that there are many suitable manners for forming the tabs 812, 814. In addition, in other embodiments, the tabs 812, 814 can be replaced by a one or more elements or protrusions attached to or formed on the interior of the proximal anchor 800.

Figure 7A:
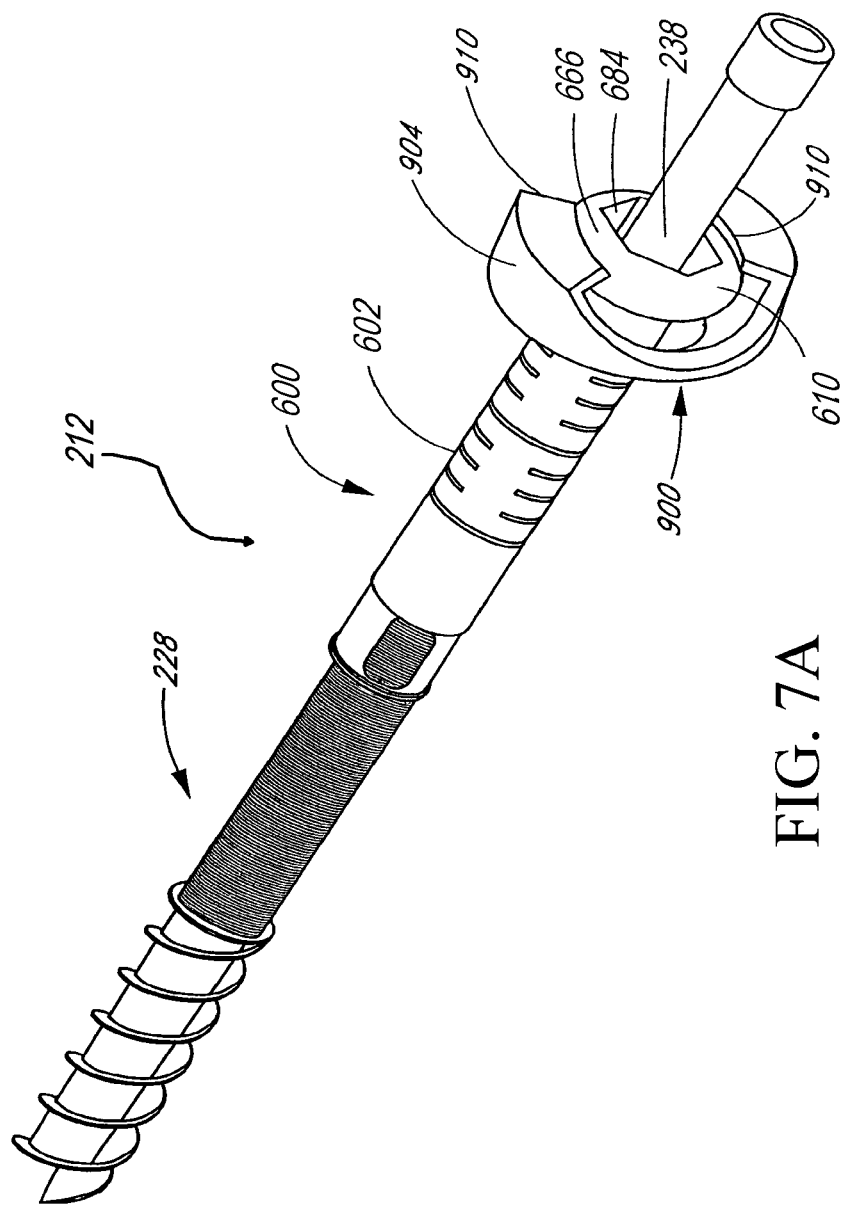
FIG. 7A is a perspective view of a washer and a fixation device.
Figure 7B:
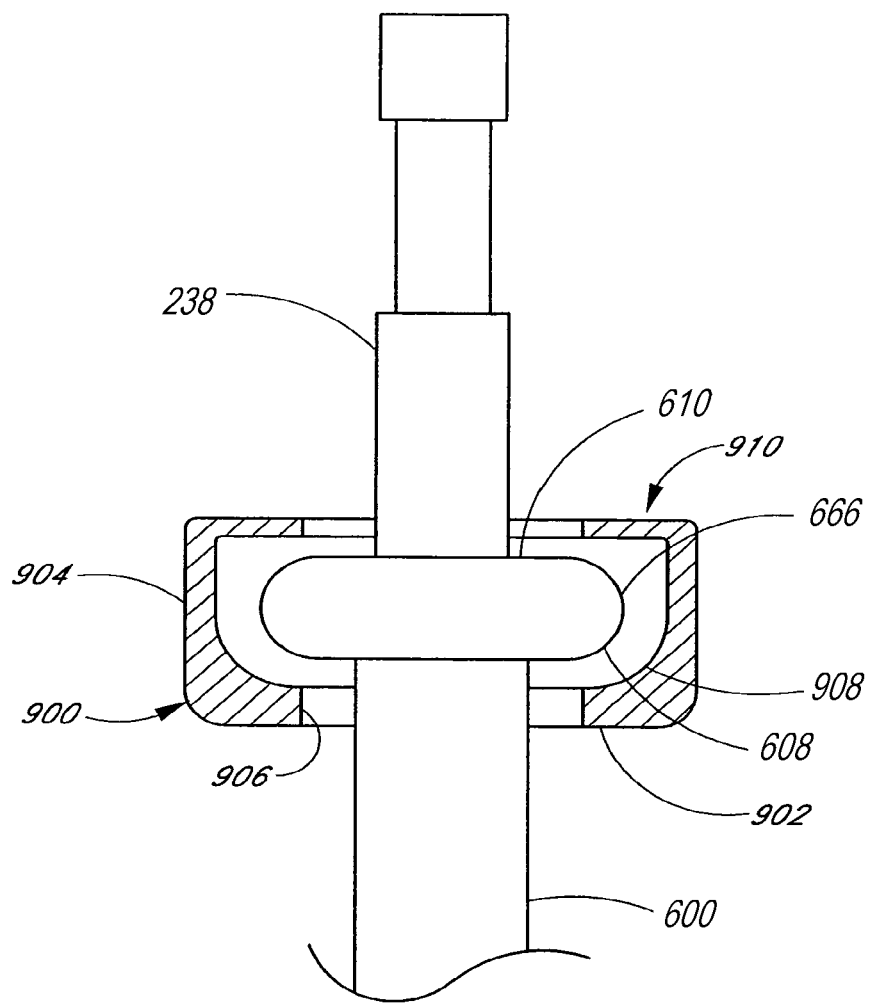
FIG. 7B is a partial cross-sectional side view of the washer of FIG. 7A and a housing of a proximal anchor.

FIGS. 7A-7B illustrate an embodiment of a fixation device 212 having a flange or washer 900. The washer 900 can be configured to interact with the flange 666 of the proximal anchor 600 of any of the embodiments described herein. The washer 900 can include a base 902 and a side wall 904. The base 902 and side wall 904 can define a curved, semi-spherical or radiused surface 908 that interacts with the corresponding curved, semi-spherical or radiused surface 608 of the flange 666. The surface 908 can surround an aperture 906 formed in the base 902. This arrangement can allow the housing 702 and/or body 228 to extend through the washer 900 and pivot with respect to the washer 900.

Figure 7C:
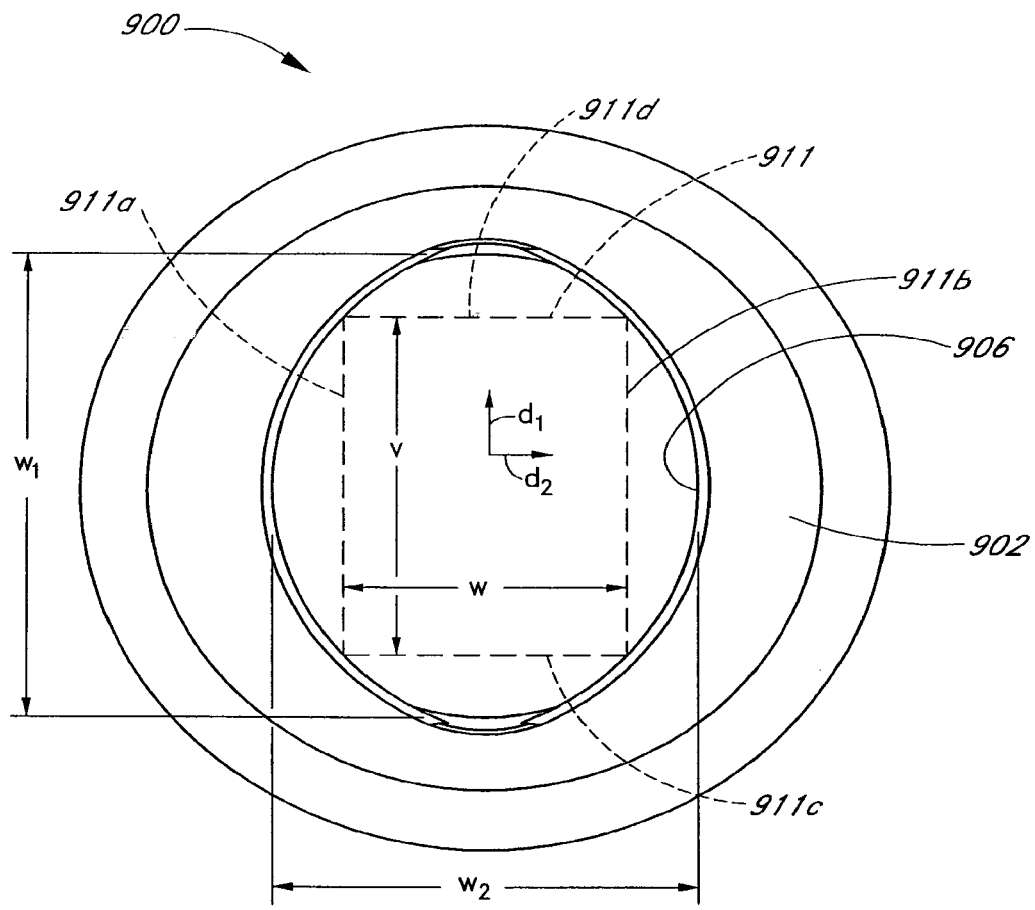
FIG. 7C is a bottom view of the washer of FIG. 7A.

With particular reference to FIG. 7C, in the illustrated embodiment, the aperture 906 is elongated with respect to a first direction d1 as compared to a second direction d2, which is generally perpendicular to the first direction d1. In this manner, the width w1 of the aperture in the first direction is greater than the width w2 of the aperture in the second direction. The aperture 906 provides a channel 911 with a width w between the sides 911a, 911b defined with respect to the second direction d2 that is preferably greater than the maximum width of the tubular housing 602 but smaller than the width of the flange 666 such that the proximal anchor 600 can not be pulled through the aperture 906. The height h of the channel is defined between the sides 911c, 911d in the second direction. As such, the elongated aperture 906 permits greater angular movement in a plane containing the first direction d1 as portions of the proximal anchor 600 are allowed rotate into the elongated portions of the aperture 906. The aperture 906 can be elliptical or formed into other shapes, such as, for example, a rectangle or a combination of straight and curved sides.

In some embodiments, the washer 900 can include a portion that is configured so that the proximal end 610 of the anchor 600 is retained, preferably permanently retained, within the washer 900. In the illustrated embodiment, the side walls 904 are provided with lips 910. The lips 910 can extend inwardly from the side walls 904 towards the aperture 906 and interact with the proximal end 610 of the flange 666 so that the proximal anchor 600 is retained within the washer 900. Preferably, the washer 900 is toleranced to allow the proximal anchor 600 to freely rotate with respect to the washer 900. In this manner, the washer 900 and the proximal anchor 600 can move together for convenient transport.

As described above, when the body 228, the proximal anchor 600 and the washer 900 are deployed into a patient, the washer 900 can inhibit distal movement of the body 228 while permitting at least limited rotation between the body 228 and the washer 900. As such, the illustrated arrangement allows for rotational and angular movement of the washer 900 with respect to the body 228 to accommodate variable anatomical angles of the bone surface. This embodiment is particularly advantageous for spinal fixation and, in particular, trans-laminar, trans-facet and trans-facet-pedicle applications. In such applications, the washer 900 can seat directly against the outer surface of a vertebra. Because the outer surface of the vertebra is typically non-planar and/or the angle of insertion is not perpendicular to the outer surface of the vertebra, a fixed flange can contact only a portion of the outer surface of the vertebra. This can cause the vertebra to crack due to high stress concentrations. In contrast, the angularly adjustable washer 900 can rotate with respect to the body and thereby the bone contacting surface can be positioned more closely to the outer surface. More bone contacting surface is thereby utilized and the stress is spread out over a larger area. In addition, the washer, which has a larger diameter than the body 228, or proximal anchor described herein, effectively increases the shaft to head diameter of the fixation device, thereby increasing the size of the loading surface and reducing stress concentrations. Additionally, the washer 900 can be self aligning with the outer surface of the vertebra, which can be curved or non-planer. The washer 900 can slide along the surface of the vertebra and freely rotate about the body 228 until the washer 900 rests snugly against the surface of the vertebra for an increased contact area between the bone and the washer 900. As such, the washer 900 can be conveniently aligned with a curved surface of the vertebra.

In some embodiments, the washer 900 can have a surface treatment or bone engagement features that can engage with the surface of the bone to inhibit relative movement between the washer 900 and the bone. The washer 900 can include a plurality of bone engagement features in the form of one or more spikes (not shown) extending from the surface of the washer 900. The spikes can contact the surface of the bone to provide additional gripping support, especially when the flange 666 is positioned against, for example, uneven bone surfaces and/or soft tissue. Optionally, the washer 900 can have protuberances, roughened surface, ridges, serrations, or other surface treatment for providing friction between the washer 900 and the surface of the bone. However, it should be appreciated that in modified embodiments the washer 900 can be formed without the bone engagement features or surface treatments. As an independent feature, for example, the washer 900 can be enlarged and includes one or two or more openings for receiving one or set screws (not shown). The setscrews can be passed through the openings to securely fasten the washer 900 to a bone.

In some embodiments, the distal anchor 234 can have a helical structure 270 for engaging cancellous bone, as illustrated in FIGS. 2A-2C. The helical structure 270, such as a flange, can either be wrapped around a central core or an axial lumen, as discussed below. The flange can extend through at least one and generally from about two to about 250 or more full revolutions depending upon the axial length of the distal anchor and intended application. For most fixation devices, the flange will generally complete from about 2 to about 20 revolutions. The helical structure 270 is preferably provided with a pitch and an axial spacing to optimize the retention force within cancellous bone, to optimize compression of the fracture. In some applications, it can advantageous for the distal anchor to engage cortical bone. In such applications, the pitch and axial spacing can be optimized for cortical bone.

In the illustrated embodiment, the helical structure 270 is shaped generally like a flat blade or radially extended screw thread. However, it should be appreciated that the helical structure 270 can have any of a variety of cross sectional shapes, such as rectangular, triangular or other as deemed desirable for a particular application through routine experimentation in view of the disclosure herein. The outer edge of the helical structure 270 defines an outer boundary. The ratio of the diameter of the outer boundary to the diameter of the central core can be optimized with respect to the desired retention force within the cancellous bone and giving due consideration to the structural integrity and strength of the distal anchor 234. Another aspect of the distal anchor 234 that can be optimized is the shape of the outer boundary and the central core, which in the illustrated embodiment are generally cylindrical with a tapered distal end 272.

The distal end 272 and/or the outer edges of the helical structure 270 can be atraumatic (e.g., blunt or soft). This inhibits the tendency of the fixation device 212 to migrate anatomically distally further into the bone after implantation. Distal migration is also inhibited by the dimensions and presence of the proximal anchor 700, which has a larger footprint than conventional screws.

Figure 8:
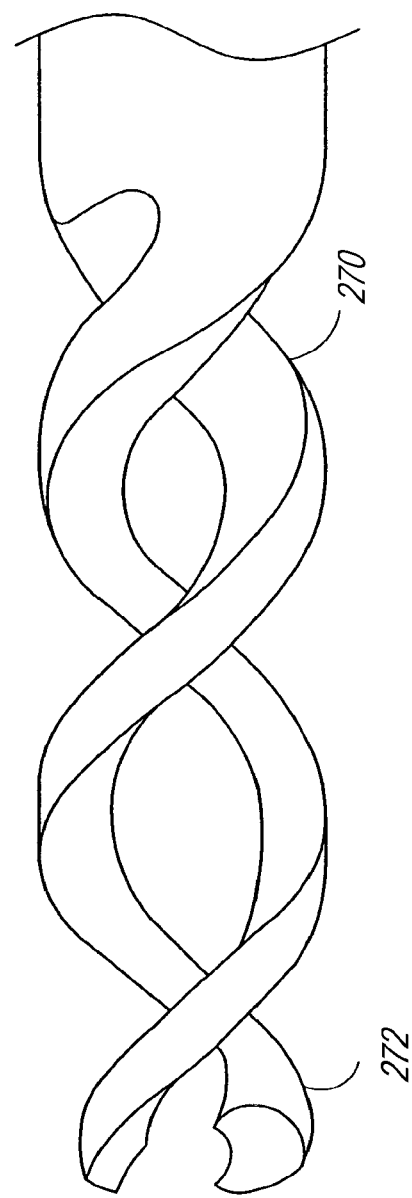
FIG. 8 is a side elevational view of a double helix distal anchor.

Referring to FIG. 8, a variation of the distal anchor 234 is illustrated. In the illustrated embodiment, the distal anchor has a double helix structure. Each helix is spirally wrapped about an imaginary cylinder through at least one and preferably from about 2 to about 20 or more full revolutions per inch. In some embodiments, each helix can be wrapped around substantially cylindrical central core that includes a central lumen that also extends through the body. The helix structure is preferably provided with pitch and an axial spacing to optimize the retention force within cancellous bone, which optimizes compression. The distal end 272 of the helical structure 270 can be pointed or sharp. In some embodiments, the helix can be wrapped about 7 revolutions per inch for an overall thread density of about 14 revolutions per inch.

Sleeve

Figure 9A:
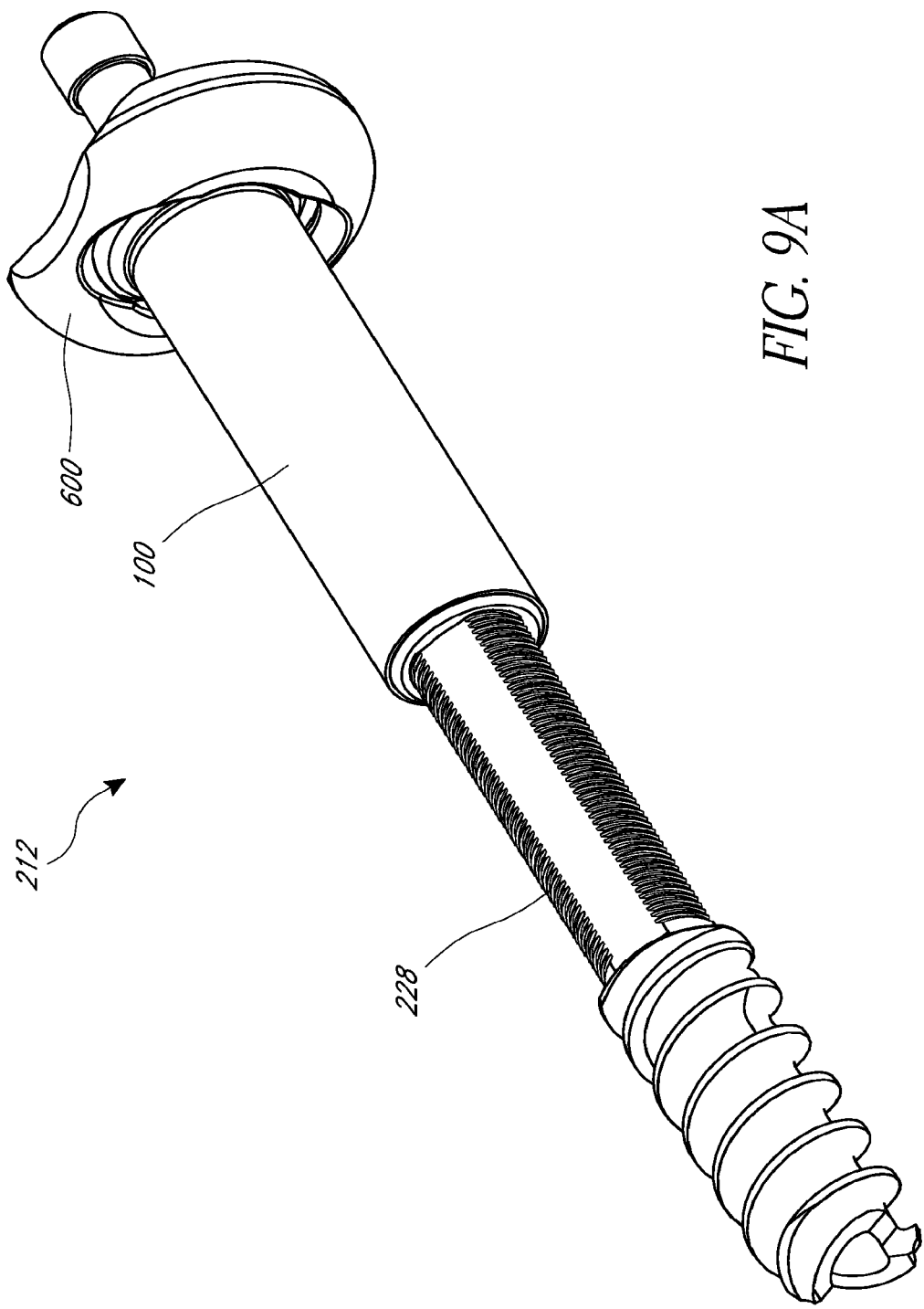
FIG. 9A is a perspective view of an embodiment of a proximal anchor with an embodiment of a sleeve.

With reference to FIG. 9A, in some embodiments, the fixation device 212 can include a sleeve 100. In the illustrated embodiment, the sleeve 100 can be tubular and be configured to be disposed around a portion of the fixation device 212. The sleeve 100 can be made of a biocompatible material and can help promote bone in-growth within a bone joint or fracture to help facilitate fusion of the bone segments. The sleeve 100 can also improve integration of the fixation device 212 with the bone. In some embodiments, the sleeve 100 can be made of materials such as allograft (e.g., cortical bone, cancellous bone, demineralized bone matrix (DBM) or bone morphogenic protein (BMP)). In certain embodiments, the sleeve 100 can be made substantially or entirely of an allograft, such as cortical bone.

In some embodiments, the sleeve 100 can be made entirely of allograft bone (e.g., cortical bone, cancellous bone and/or a combination of cortical and cancellous bone allograft). As will be described below, the use of allograft bone can beneficially promote fusion across a joint and/or a facture. However, as will be described in more detail below, other materials, or bioabsorbable or biocompatible materials can be utilized, depending upon the dimensions and desired features in other embodiments. For example, in one embodiment, the sleeve 100 is substantially made entirely of allograft bone such that over 95% of the weight of the sleeve 100 is from allograft bone, in another embodiment, over 90% of the weight of the sleeve 100 is from allograft bone and in another embodiment over 75% of the weight of the sleeve 100 is from allograft bone. In some embodiments, the sleeve 100 can be formed of allograft bone and certain portions can be formed or coated with another biocompatible or bioabsorbable material, such as, a metal (e.g., titanium), ceramics, nylon, Teflon, polymers, etc. In other embodiments, a portion of the sleeve 100 is formed from allograft bone while the remaining portions are made of another material metal (e.g., titanium), ceramics, nylon, Teflon, polymers. For example, portions of the sleeve 100 that are intended to contact the area of fusion or the facture can be formed of allograft bone with the remaining portions formed of another material (e.g., metal, ceramic, nylon, polymer etc.)

Figure 9B:
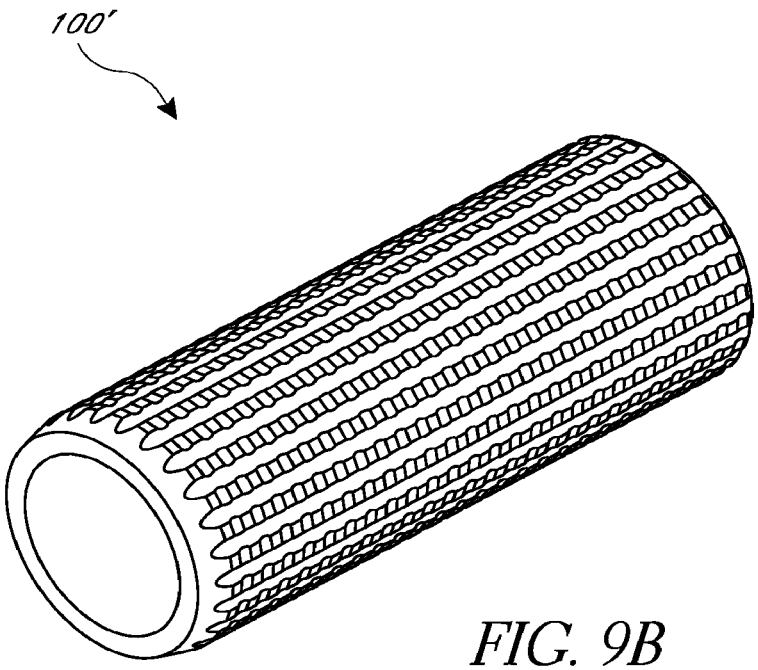
FIGS. 9B-9E are perspective views of several embodiments of sleeves having surface features.
Figure 9C:
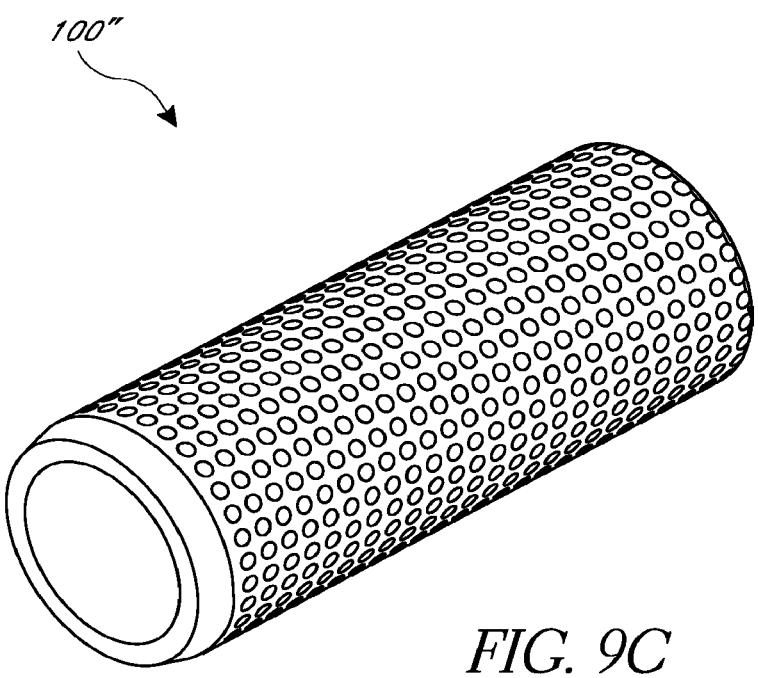
Figure 9D:
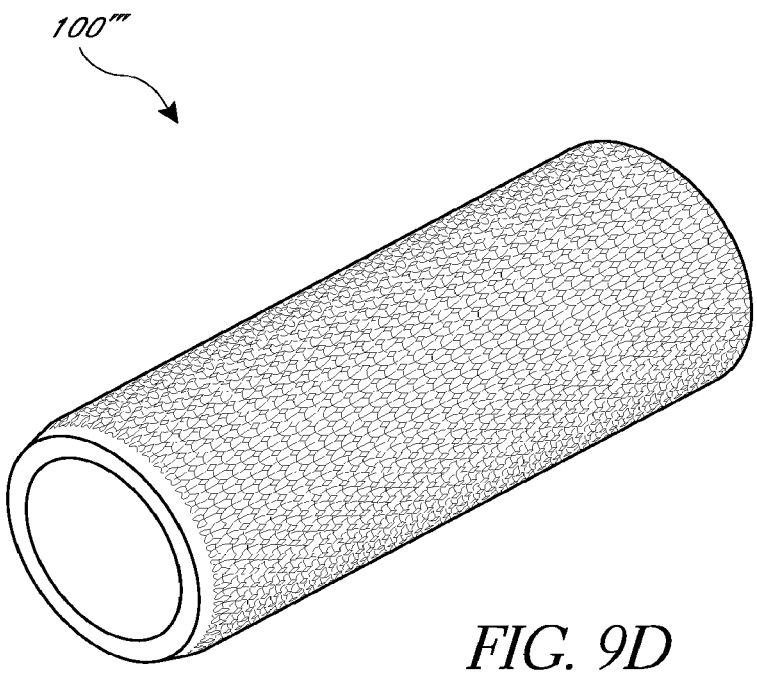
Figure 9E:
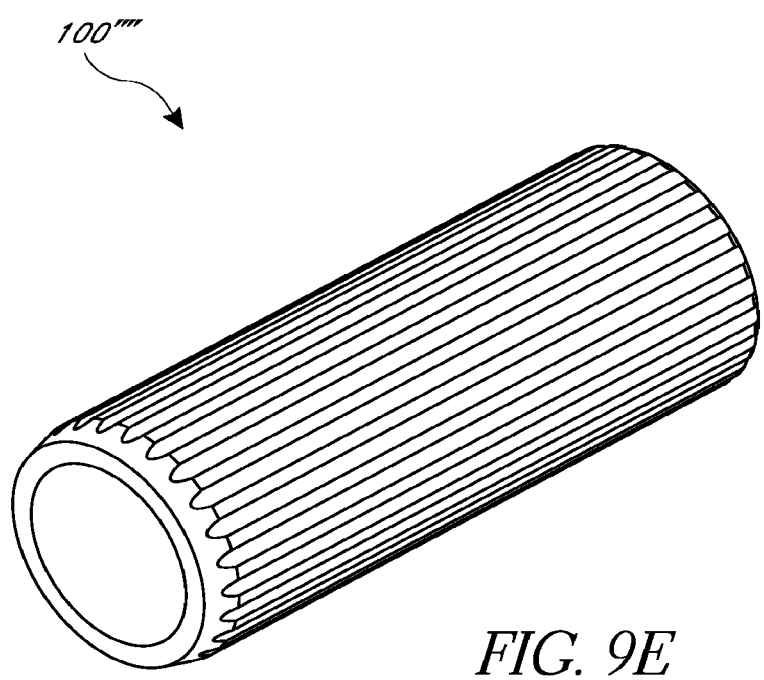

As discussed above, the sleeve 100 can help promote bone in growth and/or fusion across a bone joint and/or fracture. The sleeve 100 can be made of a material that promotes bone in-growth and can have features that also help in bone in-growth and fusion. As illustrated in FIGS. 9B-9E, the sleeve 100 can have surface features that help promote bone in-growth. The sleeve 100 can have surface features such as textures, grooves, knurling, etc. For example, FIG. 9B illustrates a sleeve 100' with longitudinal channels and circumferential grooves. FIG. 9C illustrates a sleeve 100" with dimples. In a modified embodiment, bumps or a combination of bumps and dimples could be provided. FIG. 9D illustrates a sleeve 100''' with diamond-pattern knurling. FIG. 9E illustrates a sleeve 100''' with longitudinal channels. In other embodiments, the sleeve 100 can be generally smooth. The sleeve 100 embodiments with some type of textured surface can improve osseoconduction between and along the sleeve 100 and the bone.

In some embodiments, the sleeve 100 can include other characteristics that help promote bone fusion, such as coatings, surface treatments, etc. For example, a plasma spray type of texture can be applied to the sleeve 100, which can be made of various materials, such as titanium polymers, BMP, etc.

In the embodiment illustrated in FIG. 9A, the sleeve 100 is disposed around the housing 602 of the proximal anchor 600. In other embodiments, the sleeve 100 can be disposed around the body 228 instead of, or in addition to the proximal anchor 600. Preferably, however, the sleeve 100 does not extend over the distal anchor 234 and/or distal end 232 of the fixation device 212. In some embodiments, the sleeve 100 can have a clearance or loose fit with the fixation device 212. The sleeve 100 can be assembled with the fixation device 212 just prior to being implanted. In some embodiments, the sleeve 100 can be held in place around the fixation device 212 by a friction fit. The tight fit or interference fit of the sleeve 100 over the fixation device 212 can advantageously help with osseointegration of the sleeve 100 and the fixation device 212 with the native bone, since smaller gaps help bone growth. In some embodiments, a retention material, such as adhesives can be used to hold the sleeve 100 in place on the fixation device 212. In other embodiments, the sleeve 100 can have a mating feature that couples with a complementary mating feature on the fixation device 212, such as hooks, splines, tabs, channels and grooves, or any other mating features as would be known in the art.

Figure 10A:
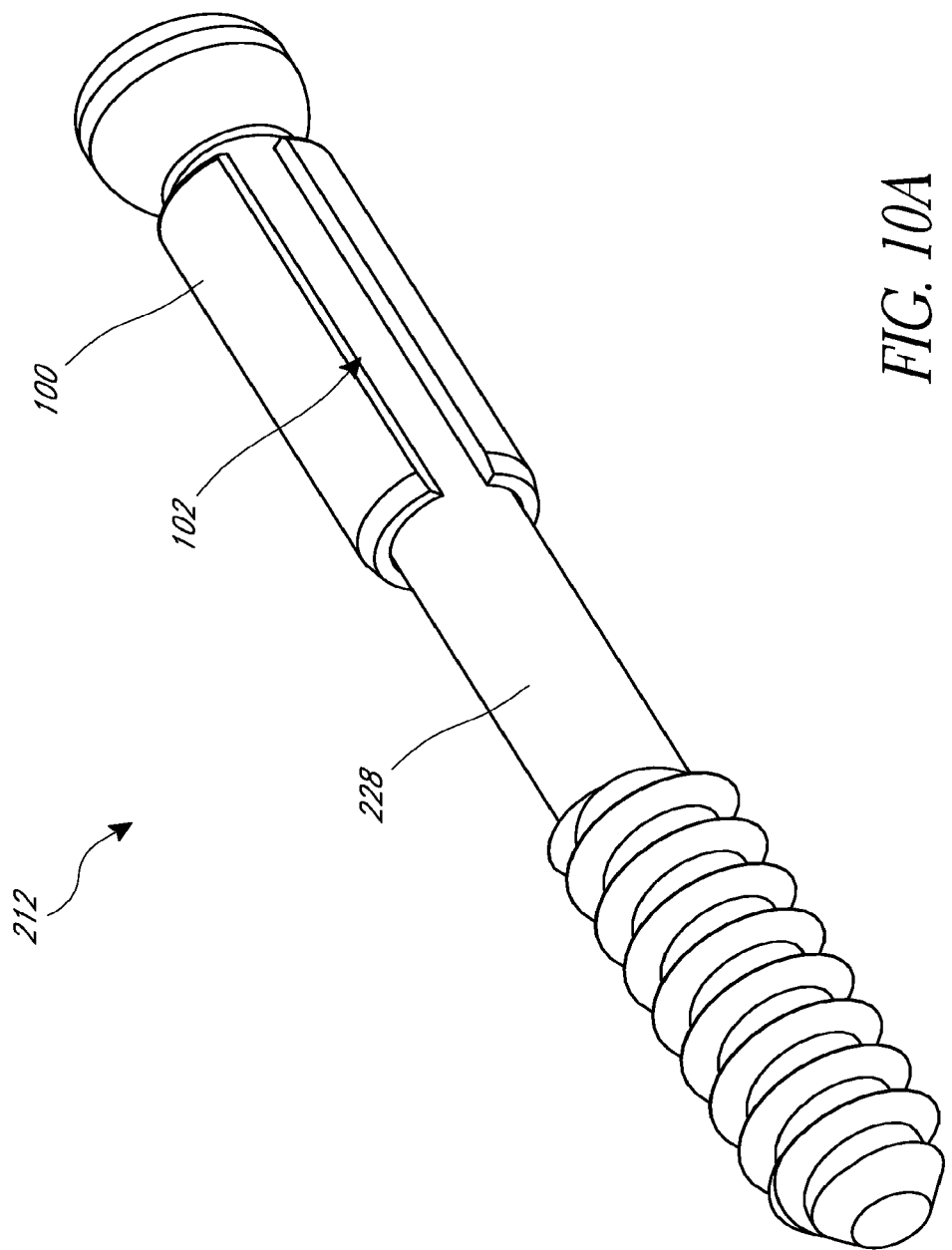
FIG. 10A is a perspective view of an embodiment of a fixation device with another embodiment of a sleeve.
Figure 10B:
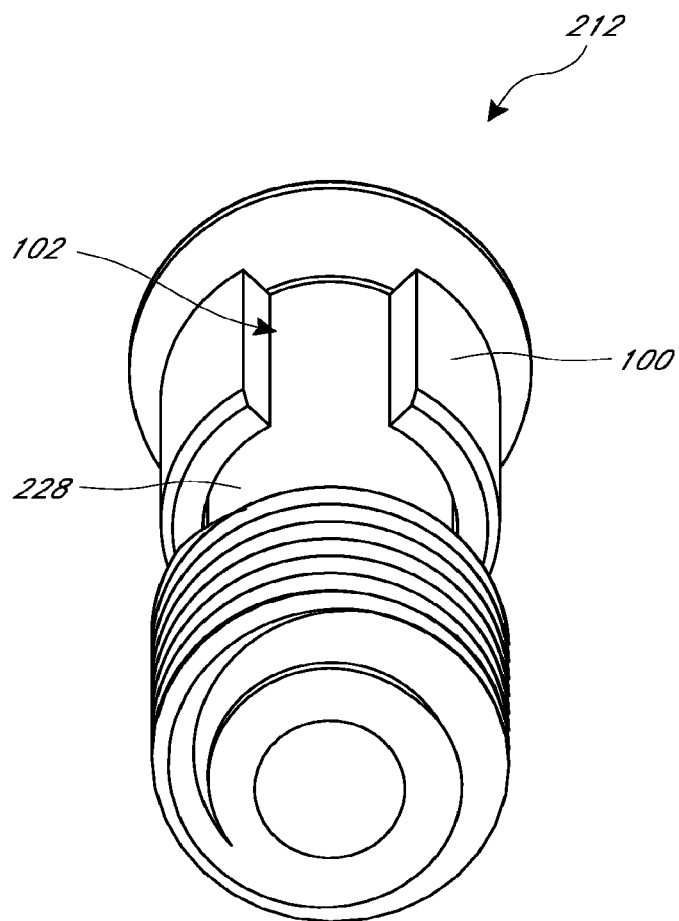
FIG. 10B is a perspective front view of the fixation device of FIG. 10A with an embodiment of a sleeve.

As illustrated in FIGS. 10A-10B, in some embodiments, the sleeve 100 can have a gap 102 extending along the longitudinal length of the sleeve 100. The gap 102 can allow the surgeon to spread the sleeve 100 open to place around the fixation device 212 from a lateral direction (i.e., from the side of the device). In other embodiments, the gap 102 can allow the device to be expanded such that it can be fit over the proximal or distal end of the device along the longitudinal axis. Such embodiments of the sleeve 100 can advantageously allow the placement of the sleeve 100 on the fixation device 212 after the fixation device 212 has already been partially implanted and/or immediately prior to implantation. For example, in one arrangement, the sleeve 100 can be prepped by a surgeon or technician and then applied to the device before the device is inserted into the patient and/or after a portion of the device has been inserted into the patient. In some embodiments, the sleeve 100 can have an inner diameter that is generally equal to or slightly smaller than the outer diameter of the body 228 of the fixation device 212, such that when the sleeve 100 is placed over the fixation device 212, the sleeve 100 can provide a compression force to form a tight fit around the body 228 of the fixation device 212. The tight fit can help promote bone in-growth inside a bone joint or fracture to help facilitate fusion of the bone segments and also promote osseoconduction, as mentioned above.

Figure 11:
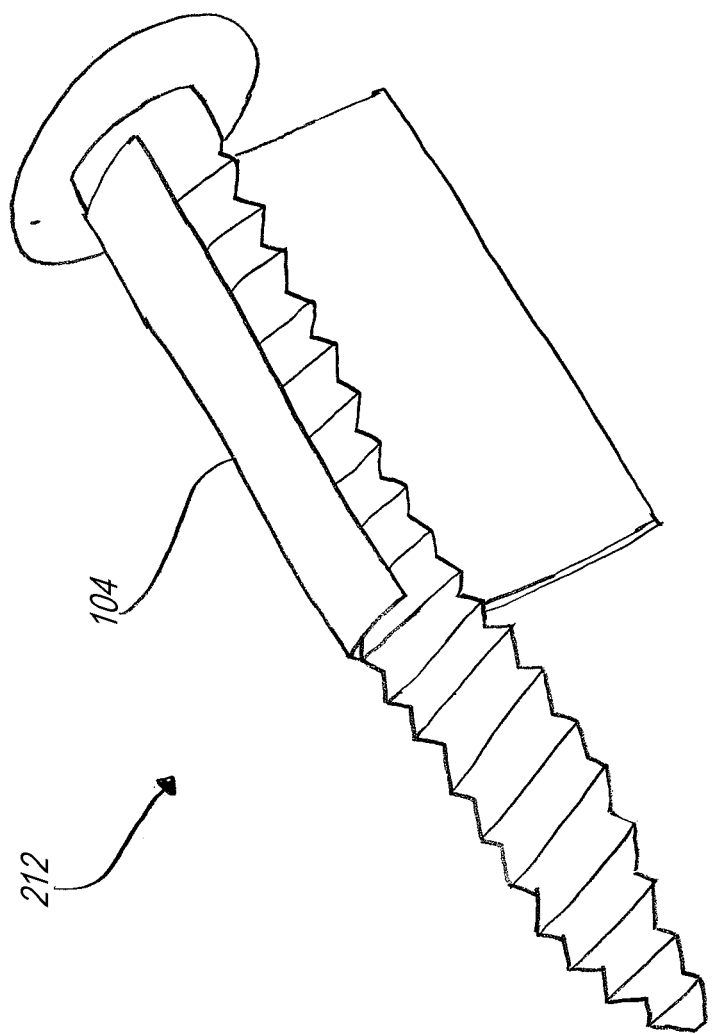
FIG. 11 is a perspective view of another embodiment of a proximal anchor with another embodiment of a sleeve.

With reference to FIG. 11, in some embodiments, the sleeve 100 can be a sheet 104 that can be wrapped around the fixation device 212. For example, a sheet of bone morphogenic protein (BMP) sponge can be wrapped around the fixation device 212 to help the fixation device integrate with the native bone. In other embodiments, the sheet can be made of other osseoconductive material, such as flexible allograft.

Although the sleeve 100 has been discussed with reference to a particular fixation device, the sleeve 100 can be used with a plurality of different types of fixation devices, such as regular screws and lag screws. For example, FIG. 11 illustrates the BMP sponge disposed around a portion of a regular fixation screw. In addition, the sleeve 100 can be used in fixation of any part of the body, such as spinal fixation, femur fixation or any other bone fixation.

In embodiments using a sleeve 100, the hole drilled for implanting the fixation device 212 during the implant procedure can be drilled slightly larger to accommodate the sleeve 100. This can be especially important when using a flexible sheet of osseoconductive material to help prevent the sheet from bunching during the procedure. However, the hole should not be drilled too large, otherwise the large gaps may hinder integration between the sleeve 100 and the bone.

Preferably, the diameter of the hole is 10% to 20% larger than the diameter of the sleeve 100 when positioned on the fixation device 212.

In some embodiments, the sleeve 100 can be coupled to the fixation device 212 before the fixation device 212 is implanted. For example, the proximal anchor 600 can be coupled with the body 228, and the sleeve 100 can be coupled to the assembled fixation device 212 prior to implantation. The entire assembly can then be implanted together into the patient. In other embodiments, the fixation device 212 can be partially implanted and the sleeve 100 can subsequently be attached. For example, the distal anchor 234 can be implanted into the bone. The sleeve 100 can be attached to the proximal anchor 600 and then the proximal anchor 600 can be compressed onto the body 228. In preferred embodiments, the sleeve 100 can be disposed over the fracture in the bone or the gap between two bones that are fixed together. For example, in trans-facet fixation, the sleeve 100 can be positioned so that it extends across the gap between the facets. The sleeve 100 can help promote bone in-growth across the fracture or gap and help strengthen the fixation. The collar 1000 can help induce bone growth within the fracture or gap and promote bone fusion. In other embodiments, the sleeve 100 is not positioned over the fracture or gap.

Spinal Fixation

Figure 12:
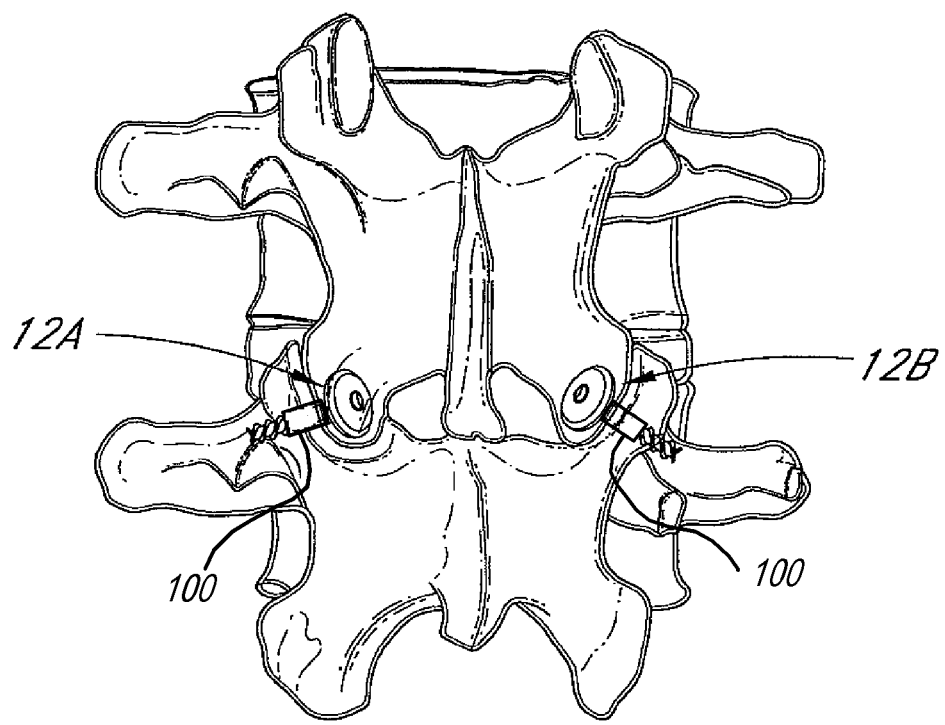
FIG. 12 is a posterior view of a portion of the lumbar spine with an embodiment of a fixation device used as a trans-facet screw.

FIG. 12 illustrates an embodiment of the fixation devices 12A, 12B implanted in the spine to provide stability. In this example, the fixation devices 12A, 12B are used as trans-facet screws. That is, the fixation devices extend through a facet of a first vertebra and into the facet of a second, typically inferior, vertebrae. As in the illustrated embodiment, this procedure is typically (but not necessarily) preformed with bilateral symmetry. Thus, even in the absence of a stabilizing bar tying pedicle screws to adjacent vertebrae or to the sacrum, and in the absence of translaminar screws that can extend through the spinous process, the fixation devices 12A, 12B can be used to stabilize two vertebrae, such as L3 and L4 to each other pending the healing of a fusion. In some embodiments, the body 228 of fixation devices 12A, 12B has a length of approximately 10 mm-30 mm and the diameter of the body is approximately 3 mm-5.5 mm.

As discussed above, a sleeve 100 can be disposed over the fixation devices 12A, 12B to help with bone in-growth within the bone joint to help facilitate fusion of the facets and can also improve integration of the fixation devices 12A, 12B with the bone. As illustrated in FIG. 12, the sleeves 100 can extend across the gap between the facets.

Figure 13:
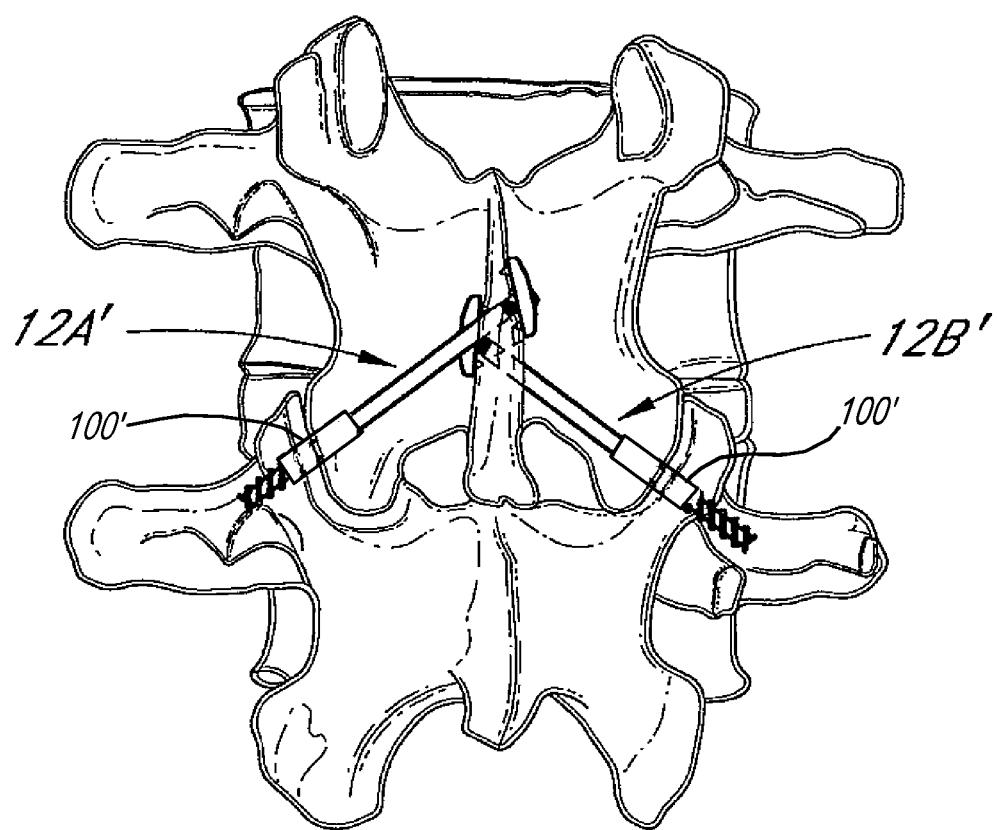
FIG. 13 is a posterior view of a portion of the lumbar spine with an embodiment of a fixation device used as a trans-facet screw.

FIG. 13 illustrates a modified arrangement for spinal fixation in which the fixation devices 12A', 12B' are used as trans-laminar facet screws. As shown in FIG. 13, in this embodiment of use, the fixation device extends through the spinous process and facet of a first vertebra and into the facet of a second, typically inferior, vertebra. As with the previous embodiment, this procedure is typically (but not necessarily) preformed with bilateral symmetry. In some embodiments, the body of fixation devices 12A', 12B' can have a length of approximately 50 mm-90 mm and the diameter of the body can be approximately 4 mm-5.5 mm. FIG. 13 illustrates a sleeve 100' disposed over the fixation devices 12A', 12B' to help with bone in-growth within the bone joint to help facilitate fusion of the facets and also improve integration of the fixation devices 12A', 12B' with the bone. In the illustrated embodiment, the sleeves 100' extend across the gap between the facets. In some embodiments it can be useful to disrupt the facet joint prior to insertion of the fixation device.

Figure 14:
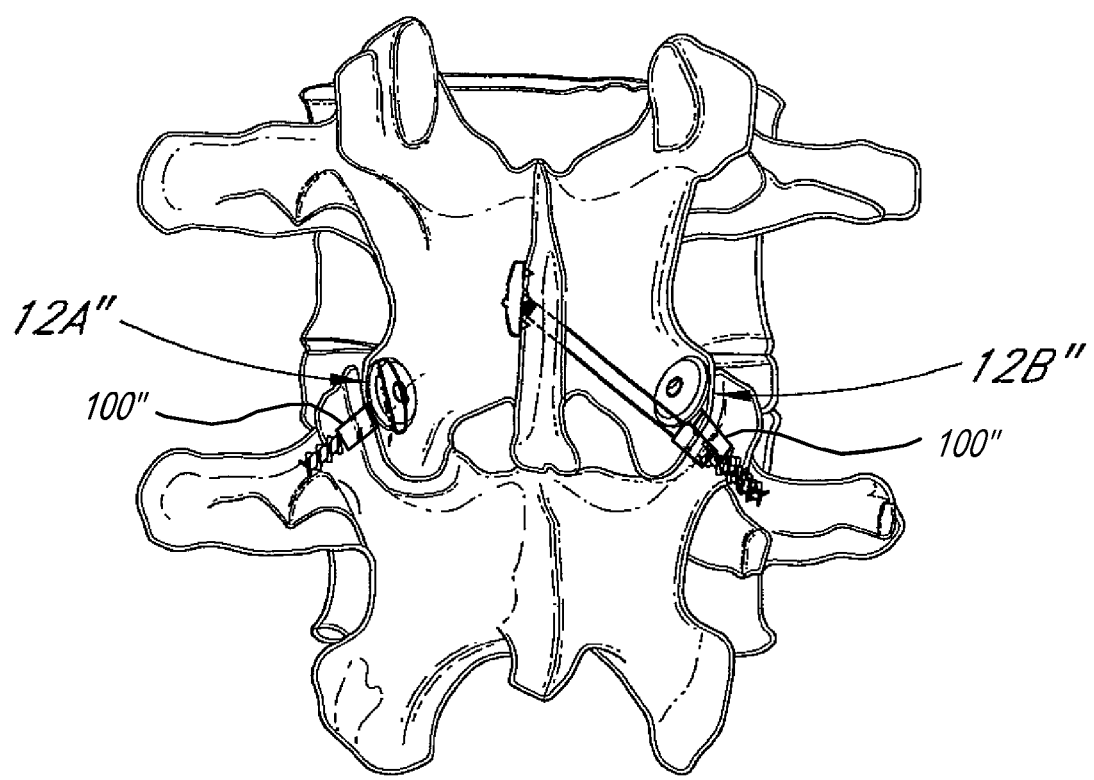
FIG. 14 is a posterior view of a portion of the lumbar spine with an embodiment of a fixation device used as a trans-facet screw.

FIG. 14 illustrates another modified arrangement for spinal fixation in which the fixation device 12A", 12B" is used as a facet-pedical screw (e.g., as used in the Boucher technique). In such an embodiment, the fixation device extends through the facet of a first vertebra and into the pedicle a second, typically inferior, vertebra. As with the previous embodiment, this procedure is typically (but not necessarily) preformed with bilateral symmetry. In such embodiments, the body of the fixation devices 12A", 12B" can be approximately 20-40 millimeters in length and approximately 3.0-5.5 millimeters in diameter. FIG. 14 illustrates a sleeve 100" disposed over the fixation devices 12A", 12B" to help with bone in-growth with the bone joint to help facilitate fusion of the facets and also improve integration of the fixation devices 12A", 12B" with the bone. In the illustrated embodiment, the sleeves 100" extend across the gap between the facets.

In some embodiments, such as illustrated in FIGS. 12-14, the flange of the proximal anchor can be supported directly against the outer surface of a vertebra. Because the outer surface is typically non-planar and/or the insertion angle of the fixation device is not perpendicular to the outer surface, an angularly fixed flange may contact only a portion of the outer surface. That is, the contact surface of the flange may not sit flush on the outer surface of the vertebra and may cause the vertebra to crack due to high stress concentrations. This can result in poor fusion rates.

As such, in these applications, the angularly adjustable washers 900 of the embodiments described with reference to FIGS. 7A-7C are particularly advantageous because the washer 900 can adjust with respect to the body and thereby the bone contacting surface can be positioned more closely to the outer surface of the vertebra. This can result in more bone contacting surface being utilized and the stress supported by the fixation device is spread out over a larger area of the vertebra. These angularly adjustable washers can also be used with the spinal cages and rods. In such embodiments, the angle of the body fixation device may not be perpendicular to the contact surface of the fixation rod or plate. In such situations, the angularly adjustable washers can allow the washers to rotate and sit flush against the fixation rod and plate.

In some embodiments, it may be advantageous to drill a counter bore into the first vertebra for receiving a portion of the proximal anchor. The counter bore can have a diameter that is slightly larger than the outer diameter of the proximal anchor so that the proximal anchor may sit at least partially below the outer surface of the vertebra.

In certain regions of the spine, the dimension transverse to a facet joint and through the adjacent facets is relatively small. In these circumstances, the fixation may desirably include a through bore, opening through the distal cortex of the distal facet. The fixation device described above can be utilized either in a blind hole application, which the distal anchor is buried within the bone, or a through bore application is which the distal helix extends into and potentially through the distal cortex.

Fractures

Figure 15:
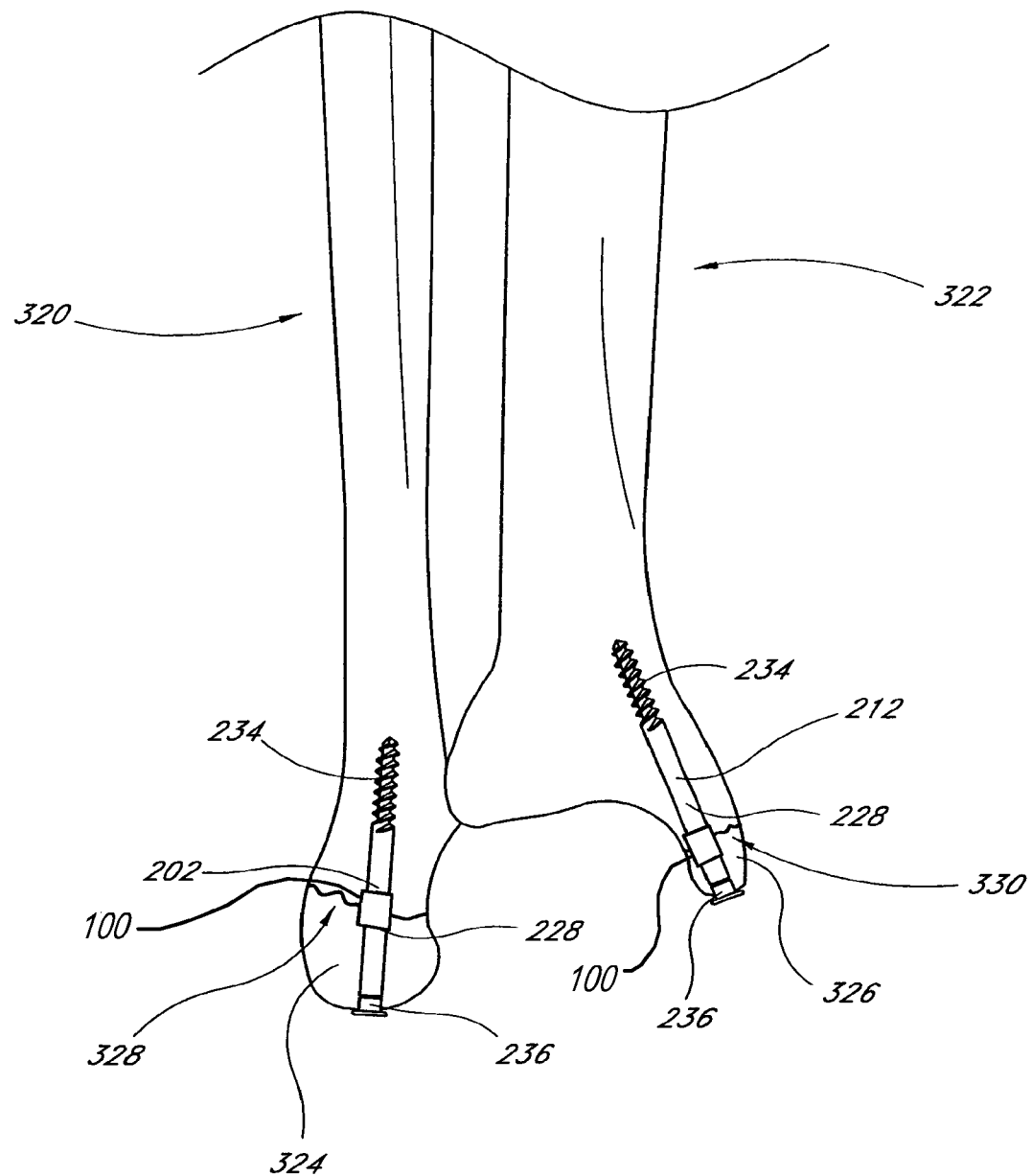
FIG. 15 is an anterior view of the distal tibia and fibula, with fixation devices across lateral and medial malleolar fractures.

FIG. 15 illustrates another embodiment of a fixation device 212 extending through the medial malleolus 326, across a medial malleolar fracture 330, and into the tibia 322. Although FIG. 15 illustrates fixation of both a lateral malleolar fracture 328 and medial malleolar fracture 330, either fracture can occur without the other as is well understood in the art. Installation of the fixation devices across malleolar fractures is accomplished utilizing the same basic steps discussed above in connection with the fixation of femoral neck fractures.

Similar to as discussed above, a sleeve 100 can be disposed over the fixation devices 212 to help with bone in-growth in the bone fracture to help facilitate fusion of the bone segments and also improve integration of the fixation devices 212 with the bone. As illustrated in FIG. 15, the sleeves 100 can extend across the fracture in the bones.

Femur

Figure 16:
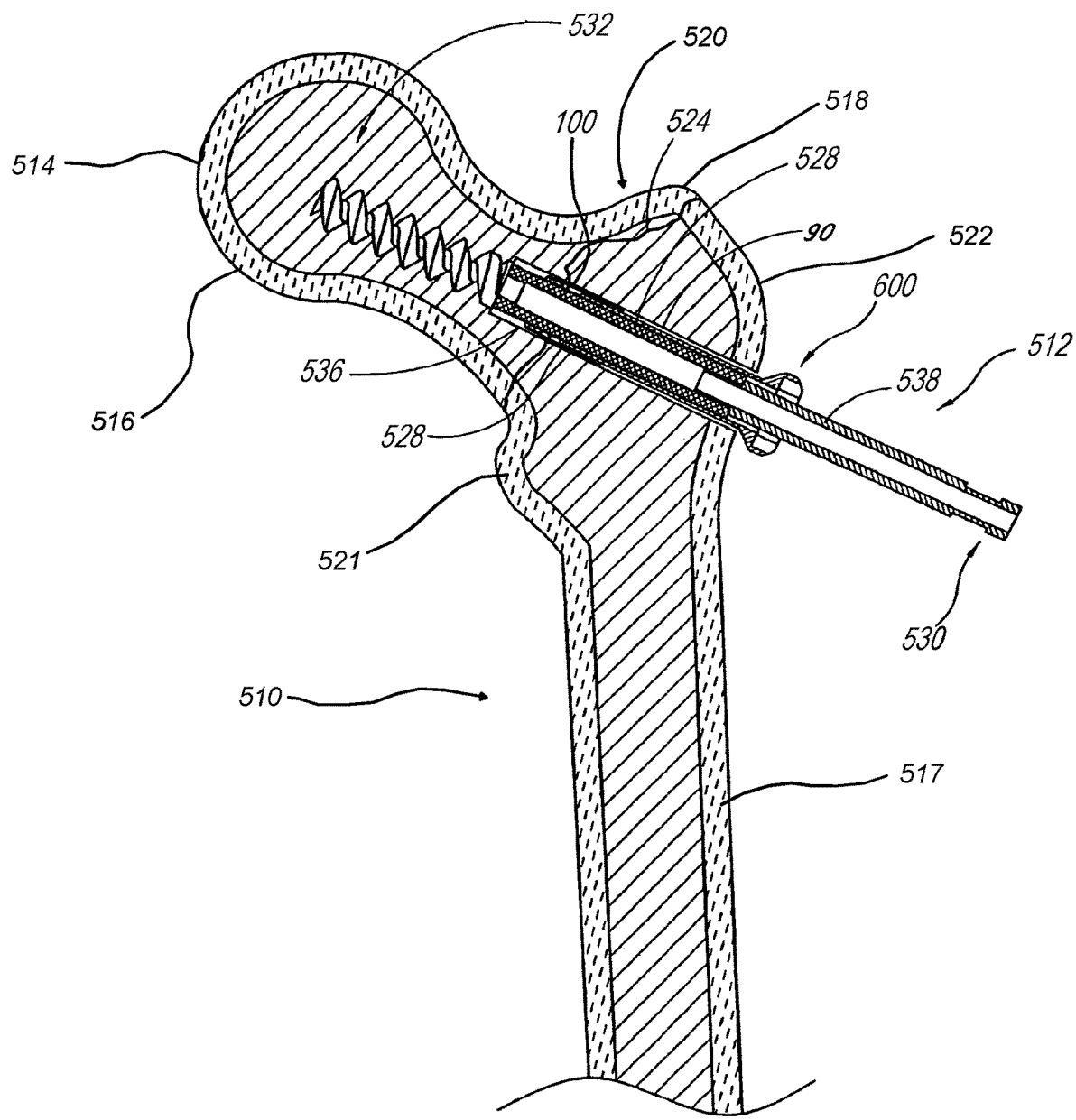
FIG. 16 illustrate a procedure for using an embodiment of a fixation device to secure a femoral neck fracture.

Referring to FIG. 16, there is illustrated a posterior side elevational view of the proximal portion of a femur 510, having a fixation device 512 positioned therein. Detailed descriptions of this and alternative fixation devices can be found in U.S. Pat. No. 6,511,481 issued on Jan. 28, 2003 entitled METHOD AND APPARATUS FOR FIXATION OF PROXIMAL FEMORAL FRACTURE, U.S. Pat. No. 6,908,465 issued on Jun. 21, 2005 entitled DISTAL BONE ANCHORS FOR BONE FIXATION WITH SECONDARY COMPRESSION and U.S. Pat. No. 6,890,333 issued on May 10, 2005 entitled METHOD AND APPARATUS FOR BONE FIXATION WITH SECONDARY COMPRESSION, which are hereby incorporated by reference herein. Although this embodiment of a fixation device 512 is disclosed in the context of fractures of the proximal femur, as with the embodiments described above, the methods and structures disclosed herein are intended for application in any of a wide variety of bones and fractures, as will be apparent to those of skill in the art in view of the disclosure herein.

The proximal end of the femur 510 comprises a head 514 connected by way of a neck 516 to the long body or shaft 517 of the femur 510. As illustrated in FIG. 16, the neck 516 is smaller in diameter than the head 514. The neck 516 and head 514 lie on an axis which, on average in humans, crosses the longitudinal axis of the body 517 of the femur 510 at an angle of about 126°. The risk of fracture at the neck 516 is elevated, among other things, by the angular departure of the neck 516 from the longitudinal axis of the body 517 of femur 510 and also the reduced diameter of the neck 516 with respect to the head 514.

The greater trochanter 518 extends outwardly above the junction of the neck 16 and the body 517 of the femur 510. On the medial side of the greater trochanter 518 is the trochanteric fossa 520. This depression accommodates the insertion of the obturator externus muscle. The lesser trochanter 521 is located posteromedially at the junction of the neck 516 and the body 517 of the femur 510. Both the greater trochanter 518 and the lesser trochanter 521 serve for the attachment of muscles. On the posterior surface of the femur 510 at about the same axial level as the lesser trochanter 521 is the gluteal tuberosity 522, for the insertion of the gluteus maximus muscle. Additional details of the femur are well understood in the art and not discussed in further detail herein.

FIG. 16 illustrates a fracture 524 which crosses the femur approximately in the area of the greater trochanter 518. Fractures of the proximal portion of the femur 510 are generally classified as capital or subcapital fractures, femoral neck fractures, intertrochanteric fractures and subtrochanteric fractures. All of these fractures will be deemed femoral neck fractures for the purpose of describing the current embodiment.

Referring to FIG. 16, the fixation device 512 can include a body 528 extending between a proximal end 530 and a distal end 532. The length, diameter and construction materials of the body 528 can be varied, depending upon the intended clinical application. In embodiments optimized for various fractures in an adult human population, the body 528 will generally be within the range of from about 10 mm to about 150 mm in length after sizing, and within the range of from about 2 mm to about 8 mm in maximum diameter. The major diameter of the helical anchor, discussed below, may be within the range of from about 2.7 mm to about 12 mm. In general, the appropriate dimensions of the body 528 will vary, depending upon the specific fracture. In rough terms, for a malleolar fracture, shaft diameters in the range of from about 3 mm to about 4.5 mm may be used, and lengths within the range of from about 25 mm to about 70 mm. For condylar fractures, shaft diameters within the range of from about 3.5 mm to about 6.5 mm may be used with lengths within the range of from about 25 mm to about 70 mm. For colles fractures (distal radius and ulna), diameters within the range of from about 2.0 mm to about 4.5 mm may be used with any of a variety of lengths within the range of from about 6 mm to about 70 mm.

In some embodiments, the body 528 can be at least partially made of titanium. However, as will be described in more detail below, other metals or bioabsorbable or nonabsorbable polymeric materials may be utilized, depending upon the dimensions and desired structural integrity of the finished fixation device 512.

The distal end 532 of the body 528 can be provided with a cancellous bone anchor or distal cortical bone anchor 534. Additional details of the distal bone anchor are described below and in U.S. Pat. No. 6,908,465 issued on Jun. 21, 2005 entitled DISTAL BONE ANCHORS FOR BONE FIXATION WITH SECONDARY COMPRESSION, which was incorporated by reference above. In general, in a femoral neck application, distal bone anchor 534 is adapted to be rotationally inserted into the cancellous bone within the head 514 of the femur 510, to retain the fixation device 512 within the femoral head.

The proximal end 530 of the fixation device 512 is provided with a proximal anchor 600. Proximal anchor 600 is axially distally moveable along the body 528, to permit compression of the fracture 524 as will be apparent from FIG. 16 and the description below. As will be explained below, complimentary locking structures such as threads or ratchet like structures between the proximal anchor 600 and the body 528 resist proximal movement of the anchor 600 with respect to the body 528 under normal use conditions. The proximal anchor 600 preferably can be axially advanced along the body 528 without rotation as will be apparent from the disclosure herein.

In the illustrated embodiment, proximal anchor 600 comprises a housing such as a tubular body, for coaxial movement along the body 528. As best seen in FIG. 16, in a final position, the housing extends distally past a junction between a first portion 536 and a second portion 538, similar to as discussed above in other embodiments. The proximal anchor 600 can have one or more surface structures for cooperating with complementary surface structures on the first portion 536 of the body 528, such as discussed above. In some embodiments, as discussed above, the proximal anchor 600 can include a washer that seats against the outer surface of the femur or tissue adjacent the femur.

As discussed above, a sleeve 100 can be disposed over the fixation device 512 to help with integration of the fixation device 512. As illustrated in FIG. 16, the sleeve 100 can extend across the gap between the facets.

Method of Use

In use, the clinician first identifies a patient having a fracture to be treated, such as a femoral neck fracture, which is fixable by an internal fixation device. With continued reference to embodiment illustrated in FIG. 16, the clinician can access the proximal femur, reduce the fracture if necessary and select a bone drill and drills a hole 90 in accordance with conventional techniques. Frequently, the hole 90 has a diameter within the range from about 3 mm to about 8 mm. This diameter may be slightly larger than the diameter of the distal anchor 34. The hole 90 preferably extends up to or slightly beyond the fracture 24. In embodiments using a sleeve 100, the hole drilled for implanting the fixation device 512 can be drilled slightly larger to accommodate the sleeve 100. However, the hole should not be drilled too large, otherwise the large gaps may hinder integration between the sleeve 100 and the bone. In one embodiment, the diameter of the hole is 10-20% than the diameter of the sleeve 100 when positioned on the fixation device 512. In certain embodiments, the clinician can use a bone drill with a counter sink configured for providing a larger diameter recesses for the housing 702 and/or the flange 244 of the proximal anchor 600.

A fixation device 512 having an axial length and outside diameter suitable for the hole 90 is selected. As discussed above, a sleeve 100 can be coupled to the fixation device 512 before the fixation device 512 is implanted. In other embodiments, the fixation device 512 can be partially implanted before the sleeve 100 is attached. The distal end 532 of the fixation device 512 can be advanced distally into the hole 90 until the distal anchor 534 reaches the distal end of the hole 90. The proximal anchor 600 can be carried by the fixation device 512 prior to advancing the body 528 into the hole 90, or can be attached following placement of the body 528 within the hole 90. Once the body 528 and proximal anchor 600 are in place, the clinician can use any of a variety of driving devices, such as electric drills or hand tools to rotate the proximal anchor 600 and thus cancellous bone anchor 534 into the head of the femur. In some embodiments, the fixation device is configured to be self-drilling or self tapping such that a hole does not have be formed before insertion into the bone.

Once the anchor 534 is in the desired location, proximal traction can be applied to the proximal end 530 of body 528, such as by conventional hemostats, pliers or a calibrated loading device, while distal force is applied to the proximal anchor 600. In this manner, the proximal anchor 600 can be advanced distally until the anchor 600 fits snugly against the outer surface of the bone or tissue adjacent the bone and the fracture 524 or space between bones can be completely reduced. Appropriate tensioning of the fixation device 512 can be accomplished by tactile feedback or through the use of a calibration device for applying a predetermined load on the implantation device. An advantage of the structure of the present embodiment is the ability to adjust compression independently of the setting of the distal anchor 534.

Following appropriate tensioning of the proximal anchor 600, the second portion 538 of the body 528 is preferably detached from the first portion 536 and removed. In the illustrated embodiment, this involves rotating the second portion 538 with respect to the first portion via the coupling, as explained above. Following removal of the second portion 538 of each body 528, the access site can be closed and dressed in accordance with conventional wound closure techniques.

An advantage of certain embodiments of the fixation devices disclosed above is that the proximal anchor can provide the device with a working range such that one device can accommodate varying distances between the distal anchor and the proximal anchor. In certain applications, this allows the technician to focus on the proper positioning of the distal anchor with the knowledge that the proximal anchor lies within the working range of the device. With the distal anchor positioned at the desired location, the proximal anchor can then be advanced along the body to compress the fracture and/or provide stability between bones. In a similar manner, the working range provides the technician with flexibility to adjust the depth of the proximal anchor. For example, in some circumstances, the bone can include voids, cysts osteoporotic bone that impairs the stability of the distal anchor in the bone. Accordingly, in some circumstances, the technician can advance the distal anchor and then desire to retract the distal anchor such that it is better positioned in the bone. In another circumstance, the technician can inadvertently advance the distal tip through the bone into a joint space. In such circumstances, the working range of the device allows the technician to reverse and retract the anchor and recompress connection. Such adjustments are facilitated by the working range of the proximal anchor on the body.

In one embodiment, the clinician will have access to an array of fixation devices having, for example, different diameters, axial lengths and angular relationships. These can be packaged one per package in sterile envelopes or peelable pouches, or in dispensing cartridges which can each hold a plurality of devices. Upon encountering a fracture for which the use of a fixation device is deemed appropriate, the clinician will assess the dimensions and load requirements, and select a fixation device from the array which meets the desired specifications.

As noted above, in spinal fixation applications, the fixation device 12 can be used as a trans-facet screw. That is, the fixation device extends through a facet of a first vertebra and into the facet of a second, typically inferior, vertebrae. This procedure is typically (but not necessarily) preformed with bilateral symmetry. Thus, even in the absence of a stabilizing bar tying pedicle screws to adjacent vertebrae or to the sacrum, and in the absence of translaminar screws that can extend through the spinous process, the fixation devices can be used to stabilize two vertebrae, such as L3 and L4 to each other pending the healing of a fusion. In some embodiments, the body 28 of fixation device 12 can have a length of approximately 10 mm-30 mm and the diameter of the body is approximately 3 mm to 5.5 mm.

The fixation device 12 can also be used as a trans-laminar facet screw. In this embodiment of use, the fixation device can extend through the spinous process and facet of a first vertebra and into the facet of a second, typically inferior, vertebra. As with the previous embodiment, this procedure is typically (but not necessarily) preformed with bilateral symmetry. In some embodiments, the body 28 of fixation device 12 can have a length of approximately 50 mm-90 mm and the diameter of the body is approximately 4 mm to 5.5 mm.

The fixation device can also be used is used as a facet-pedical screw (e.g., as used in the Boucher technique). In such embodiments, the fixation device extends through the facet of a first vertebra and into the pedicle a second, typically inferior, vertebra. As with the previous embodiment, this procedure is typically (but not necessarily) preformed with bilateral symmetry. In such embodiments, the fixation device 12 and the body 28 can be approximately 20-40 millimeters in length and 3.0-5.5 millimeters in diameter.

The specific dimensions of any of the bone fixation devices described herein can be readily varied depending upon the intended application, as will be apparent to those of skill in the art in view of the disclosure herein. Moreover, although the present invention has been described in terms of certain preferred embodiments, other embodiments of the invention including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and subcombinations. The use of different terms or reference numerals for similar features in different embodiments does not imply differences other than those which can be expressly set forth. Accordingly, the present invention is intended to be described solely by reference to the appended claims, and not limited to the preferred embodiments disclosed herein.

I claim:

1. An orthopedic fixation device comprising:
an elongate body having a proximal end and a distal end;
a distal anchor on the distal end;
a proximal anchor on the proximal end, wherein the proximal anchor is rotatably fixed relative to the distal anchor such that rotation of the proximal anchor in a first rotation direction rotates the distal anchor in the first rotation direction; and
a sleeve covering at least a portion of the fixation device, wherein the sleeve comprises a material configured to promote fusion within a joint or fracture, and wherein the sleeve is movable relative to the entire proximal anchor and the entire elongate body,
wherein the proximal anchor defines a radially outwardly extending portion that extends radially, away from a longitudinal axis defined by the elongate body, beyond the sleeve or the distal anchor,
wherein the proximal anchor is moveably carried on the elongate body, the proximal anchor comprising at least one complementary retention structure configured for permitting proximal movement of the elongate body with respect to the proximal anchor but resisting distal movement of the elongate body with respect to the proximal anchor, and
wherein the sleeve comprises a longitudinal slit configured to allow the sleeve to expand and fit around at least the portion of the fixation device.

2. The orthopedic fixation device of claim 1, wherein the sleeve is made substantially of bone allograft.

3. The orthopedic fixation device of claim 1, wherein the sleeve comprises a biocompatible sponge sheet that is wrapped around the fixation device.

4. The orthopedic fixation device of claim 1, wherein the distal anchor comprises a helical flange.

5. The orthopedic fixation device of claim 1, wherein the proximal anchor is a monolithic body that directly engages the elongate body.

6. The orthopedic fixation device of claim 1, wherein the sleeve is separable from the proximal anchor.

7. The orthopedic fixation device of claim 1, wherein the sleeve is translationally movable relative to the entire proximal anchor and the entire elongate body.

8. The orthopedic fixation device of claim 1, wherein the radially outwardly extending portion extends radially, away from the longitudinal axis, beyond the sleeve.

9. An orthopedic fixation device comprising:
an elongate body having a proximal end and a distal end;
a distal anchor on the distal end;
a proximal anchor on the proximal end, wherein the proximal anchor is a monolithic body that movably and directly engages the elongate body; and
a sleeve covering at least a portion of the elongate body and at least a portion of the proximal anchor, wherein the sleeve comprises a material configured to promote fusion within a joint or fracture,
wherein the sleeve comprises a longitudinal slit configured to allow the sleeve to expand and fit around the fixation device.

10. The orthopedic fixation device of claim 9, wherein the sleeve is made substantially of bone allograft.

11. The orthopedic fixation device of claim 9, wherein the proximal anchor is moveably carried on the elongate body, the proximal anchor comprising at least one complementary retention structure configured for permitting proximal movement of the elongate body with respect to the proximal anchor but resisting distal movement of the elongate body with respect to the proximal anchor.

12. The orthopedic fixation device of claim 9, further comprising an adhesive between the sleeve and at least a portion of the fixation device.

13. The orthopedic fixation device of claim 9, wherein the sleeve is separable from the proximal anchor.

14. The orthopedic fixation device of claim 9, wherein the monolithic body directly engages a surface defined by the elongate body.

15. An orthopedic fixation device comprising:
an elongate body having a proximal end and a distal end;
a distal anchor on the distal end;
a proximal anchor on the proximal end;
a sleeve covering at least a portion of the fixation device, wherein the sleeve comprises a material configured to promote fusion within a joint or fracture; and
an adhesive between the sleeve and the portion of the fixation device that positionally fixes the sleeve to the portion of the fixation device,
wherein the proximal anchor defines a radially outwardly extending portion that extends radially, away from a longitudinal axis defined by the elongate body, beyond the sleeve or the distal anchor,
wherein the sleeve extends radially, away from the longitudinal axis, beyond a majority of a radially outermost surface of the elongate body, and
wherein the proximal anchor and the sleeve define distinct bodies.

16. The orthopedic fixation device of claim 15, wherein the sleeve is made substantially of bone allograft.

17. The orthopedic fixation device of claim 15, wherein the sleeve comprises a longitudinal slit configured to allow the sleeve to expand and fit around the fixation device.

18. The orthopedic fixation device of claim 15, wherein the proximal anchor is a monolithic body that directly engages the elongate body.

19. The orthopedic fixation device of claim 15, wherein the sleeve comprises a smooth interior surface that faces toward the portion of the fixation device.

* * * * *